(12) United States Patent
Nickel

(10) Patent No.: US 11,326,195 B2
(45) Date of Patent: May 10, 2022

(54) STARCH-DERIVED CLATHRATE-FORMING COMPOSITIONS

(71) Applicant: Gary B. Nickel, Panama (PA)

(72) Inventor: Gary B. Nickel, Panama (PA)

( * ) Notice: Subject to any disclaimer, the term of this patent is extended or adjusted under 35 U.S.C. 154(b) by 197 days.

(21) Appl. No.: 16/590,954

(22) Filed: Oct. 2, 2019

(65) Prior Publication Data

US 2020/0392548 A1     Dec. 17, 2020

Related U.S. Application Data

(63) Continuation of application No. PCT/US2019/046671, filed on Aug. 15, 2019.

(60) Provisional application No. 62/861,426, filed on Jun. 14, 2019.

(51) Int. Cl.
| | |
|---|---|
| *C12P 19/14* | (2006.01) |
| *A61K 9/10* | (2006.01) |
| *C12P 19/16* | (2006.01) |
| *C08B 30/18* | (2006.01) |
| *A61K 31/05* | (2006.01) |

(52) U.S. Cl.
CPC ............... *C12P 19/14* (2013.01); *A61K 9/10* (2013.01); *A61K 31/05* (2013.01); *C08B 30/18* (2013.01); *C12P 19/16* (2013.01); *C12Y 302/01001* (2013.01)

(58) Field of Classification Search
CPC .... A61K 31/05; A61K 31/355; A61K 31/404; A61K 31/593; A61K 9/10; C08B 30/20; C08B 30/18; C12P 19/14; C12P 19/16
See application file for complete search history.

(56) References Cited

U.S. PATENT DOCUMENTS

| 4,384,898 A | 5/1983 | Okada et al. |
| 7,550,279 B2 | 6/2009 | Nickel |
| 2015/0050384 A1 | 2/2015 | Nickel |

FOREIGN PATENT DOCUMENTS

WO       199417676 A1    8/1992

OTHER PUBLICATIONS

Wang et al., J. Agric. Food Chem., 2017, 65, p. 8744-8753. (Year: 2017).*
"International Search Report & Written Opinion for PCT/US2019/046671, dated Oct. 24, 2019".
Bijttebier, et al., "Amylase Action Pattern on Starch Polymers", Institute of Molecular Biology, Slovak Academy of sciences, 2008, 989-999.
Hii, et al., "Pullulanase: Role in Starch Hydrolysis and Potential Industrial Applications", Hindawi Publishing Corporation, Enzyme Research, vol. 2012, Article ID 921362, 2012, 1-14.

* cited by examiner

*Primary Examiner* — Jonathan S Lau
(74) *Attorney, Agent, or Firm* — Billion & Armitage

(57) ABSTRACT

Embodiments of the present disclosure relate to materials and methods for preparing a clathrate-forming composition comprising a plurality of linear glucomonomer chains of about 15 to about 100 D-glucopyranosyl residues linked by α-1,4 linkages, wherein the linear glucomonomer chains are a product of partial amylolysis of a modified starch substrate and wherein the product is flowable at temperatures within a range of 4-20° C. at about 20% w/v solids content. The present disclosure further describes methods of using the clathrate-forming compositions to form molecular dispersions or clathrates with hydrophobic guest molecules, kits for use in these methods, and molecular dispersions or clathrates obtained from the materials.

10 Claims, 22 Drawing Sheets

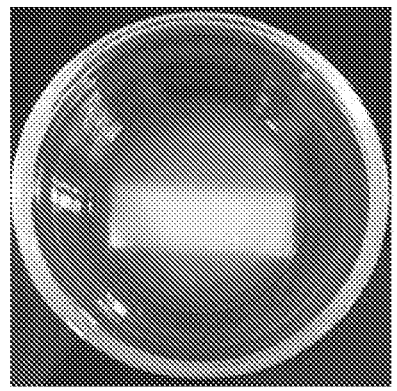
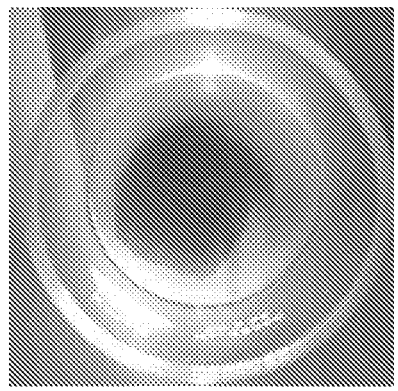
FIG. 9A  FIG. 9B
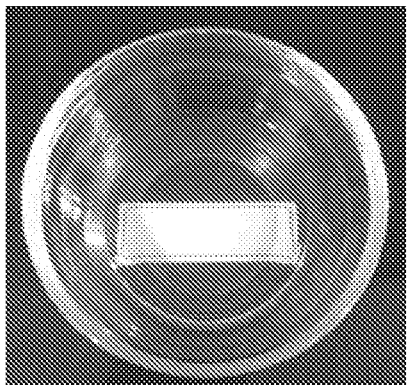
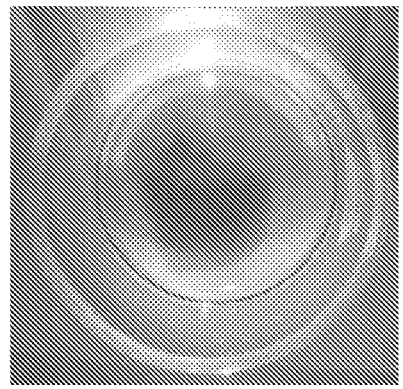
FIG. 9C  FIG. 9D

STARCH-DERIVED CLATHRATE-FORMING COMPOSITIONS

BACKGROUND

Starch is a naturally produced, abundantly available, and widely used polysaccharide material. Starch is produced in discrete granules, which are almost entirely composed of two major polysaccharides: amylose and amylopectin. Both polysaccharides include linear chains of α-(1,4)-linked D-glucose residues. In amylopectin, these linear chains are interconnected through α-(1,6)-glucosidic linkages, forming branches in the polymer. Generally, amylose chains include several hundreds or even thousand glucosyl units, whereas amylopectin is extensively branched with comparatively short chains. The different quantity and organizational distribution of amylose and amylopectin leads to diverse starch compositions, affecting their structures and functions. This diversity can complicate the utility of starch for industrial applications.

Processes of modifying starch chemically and enzymatically to expand and exploit the range of its functional properties have been used in a several industrial areas, and particularly in food production. For example, U.S. Pat. No. 7,550,279 describes methods of harvesting clathrate-forming amylose material from modified starch for use in food products, however the resulting compositions include an array of products of starch hydrolysis, some of which limit the ability of the harvested material to form host:guest complexes suitable for non-food applications, such as compositions for therapeutic use.

There is a need in the art for materials and methods that further expand the utility of starch for complexing various poorly water soluble, or water insoluble hydrophobic agents. Methods capable of releasing, concentrating and/or isolating the different fractions of clathrate-forming materials present within starch are needed for the development of new host:guest complexes and delivery formulations. There is a need for clathrate-forming compositions that can be tailored for formulation in specific delivery vehicles or with specific release profiles to improve the bioavailability of hydrophobic guest molecules with therapeutic, nutraceutical, or cosmeceutical activity.

SUMMARY

In general, the present disclosure features materials and methods for providing starch-derived clathrate-forming compositions. Embodiments of these methods include strategic control of reaction conditions to release specific clathrate-forming molecules, referred to herein as "amylettes", from starch. Further embodiments selectively target contaminating molecules, such as amylopectin and cell wall polysaccharides, for degradation, thereby protecting "amylettes" for concentration and/or isolation efficiency. The clathrate-forming compositions can enhance delivery of poorly water soluble, or water insoluble hydrophobic therapeutic, nutraceutical, or cosmeceutical active agents through the formation of molecular dispersions, host:guest complexes, and/or inclusion compounds.

Embodiments of the present disclosure describe methods for preparing a clathrate-forming composition comprising a plurality of linear glucomonomer chains of about 15 to about 100 D-glucopyranosyl residues linked by α-1,4 linkages, wherein the chains are a product of partial amylolysis of a modified starch substrate and wherein the product is flowable at temperatures within a range of 4-20° C. at about 20% w/v solids content, methods of using the clathrate-forming compositions to complex hydrophobic guest molecules, kits for use in these methods, molecular dispersions of hydrophobic guest molecules comprising a clathrate-forming composition, and host:guest complexes comprising one or more of the clathrate-forming compositions.

Thus, a first aspect of the present disclosure features a clathrate-forming composition comprising a plurality of linear glucomonomer chains of about 15 to about 100 D-glucopyranosyl residues linked by α-1,4 linkages, wherein the linear glucomonomer chains are a product of partial amylolysis of a modified starch substrate, wherein the partially amylolyzed product is flowable at temperatures within a range of 4-20° C. at about 20% w/v solids content. The composition can be substantially free of amylopectin and remnants of amylopectin. Any of the compositions described above can be substantially free of amylopectin and remnants of amylopectin. Any of the compositions described above can be substantially free of amylose molecules having a chain length greater than 250 glucomonomers. In any of the compositions described above at least one of the glucomonomer chains can be esterified. The esterified glucomonomer chain can be esterified with an acylating agent, a fatty acid, or a combination thereof. The esterified glucomonomer chain can be esterified with a fatty acid selected from the group consisting of saturated or unsaturated straight chain fatty acids having up to 30 carbon atoms, saturated or unsaturated branched fatty acids having 4 to 26 carbon atoms, and a combination thereof. In any of the compositions described above, a dynamic viscosity of the product having a solids content of 20% w/v is less than 2300 mPa·s as measured on a rotary viscometer with spindle 1 operated at a speed of about 0.3 rpm at temperatures within a range of 4-20° C. In any of the compositions described above, the composition further comprises a hydrophobic guest molecule. The hydrophobic guest molecule is selected from the group consisting of resveratrol, vitamin E, vitamin D, quercetin, diindolylmethane, coenzyme Q10, and cannabidiol (CBD).

A second aspect of the present disclosure describes a method of preparing a clathrate-forming composition comprising: thinning a modified starch substrate paste by a first partial amylolysis step including endo-α-amylase digestion of the modified starch substrate under reaction conditions that restrain enzyme activity to less than 60% relative activity to provide a first product comprising a plurality of linear glucomonomer chains of about 15 to about 100 D-glucopyranosyl residues linked by α-1,4 linkages; wherein the first product is flowable at temperatures within a range of 4-20° C. at about 20% w/v solids content. The method can further comprising preparing the modified starch substrate paste by: soaking a starch substrate in an aqueous alkaline solution having a pH greater than 10.5; modifying the soaked starch substrate by esterification with an acylating agent; and hydrating the modified starch substrate to fully gelatinize the modified starch substrate. Any of the methods described above can further comprise thinning the first product by a second partial amylolysis including endo-α-amylase digestion of the first product under reaction conditions that restrain enzyme activity to less than 30% relative activity to provide a second product having a lower dynamic viscosity than the first product within a temperature range of 4-20° C.; wherein the second product comprises a plurality of linear glucomonomer chains of about 15 to about 100 D-glucopyranosyl residues linked by α-1,4 linkages. The method can further comprise dispersing a hydrophobic guest molecule in the second product. One or more of the methods described above can include degrading amylopectin released by thinning the modified starch paste by amylolysis. Any of the methods described above can further comprise separating amylose molecules having a chain length greater than 250 glucomonomers from the linear glucomonomer chains of about 15 to about 100 D-glucopyranosyl residues linked by α-1,4 linkages. Any of the methods described above can further comprise esterifying the plurality of linear glucomonomer chains to form a composition comprising esterified clathrate-forming molecules. The method can further comprise dispersing a hydrophobic guest molecule in the composition comprising esterified clathrate-forming molecules. According to one or more of the methods described above the hydrophobic guest molecule is selected from the group consisting of resveratrol, vitamin E, vitamin D, quercetin, diindolylmethane, coenzyme Q10, and cannabidiol (CBD).

A third aspect of the present disclosure describes a kit for forming a clathrate with a hydrophobic guest molecule comprising: a first container comprising a clathrate-forming composition comprising a plurality of linear glucomonomer chains of about 15 to about 100 D-glucopyranosyl residues linked by α-1,4 linkages, wherein the linear glucomonomer chains are a product of partial amylolysis of a modified starch substrate and wherein the product is flowable at temperatures within a range of 4-20° C. at about 20% w/v solids content; a second container comprising a hydrophobic guest molecule; and instructions for preparing the clathrate. The kit can include a third container comprising a plurality of amylose chains having a degree of polymerization of at least 250; and instructions for wrapping the clathrate in the amylose chains.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document. The patent or application file contains at least one drawing executed in color. Copies of this patent or patent application publication with color drawings will be provided by the Office upon request and payment of the necessary fee.

Reference is made to illustrative embodiments that are depicted in the figures, in which:

FIGS. 9A-F describe Amylettes Product 3A, according to one or more embodiments of the present disclosure. (A) shows a color image of Amylettes Product 3A at 4° C.; (B) shows a color image of Amylettes Product 3A at 4° C. after addition of iodine; (C) shows a color image of Amylettes Product 3A at 20° C.; (D) shows a color image of Amylettes Product 3A at 20° C. after addition of iodine; (E) and (F) show the dynamic viscosity of Product 3A at different spindle speeds measured at 4° C. or 25° C., respectively.

DETAILED DESCRIPTION

Figure 1:
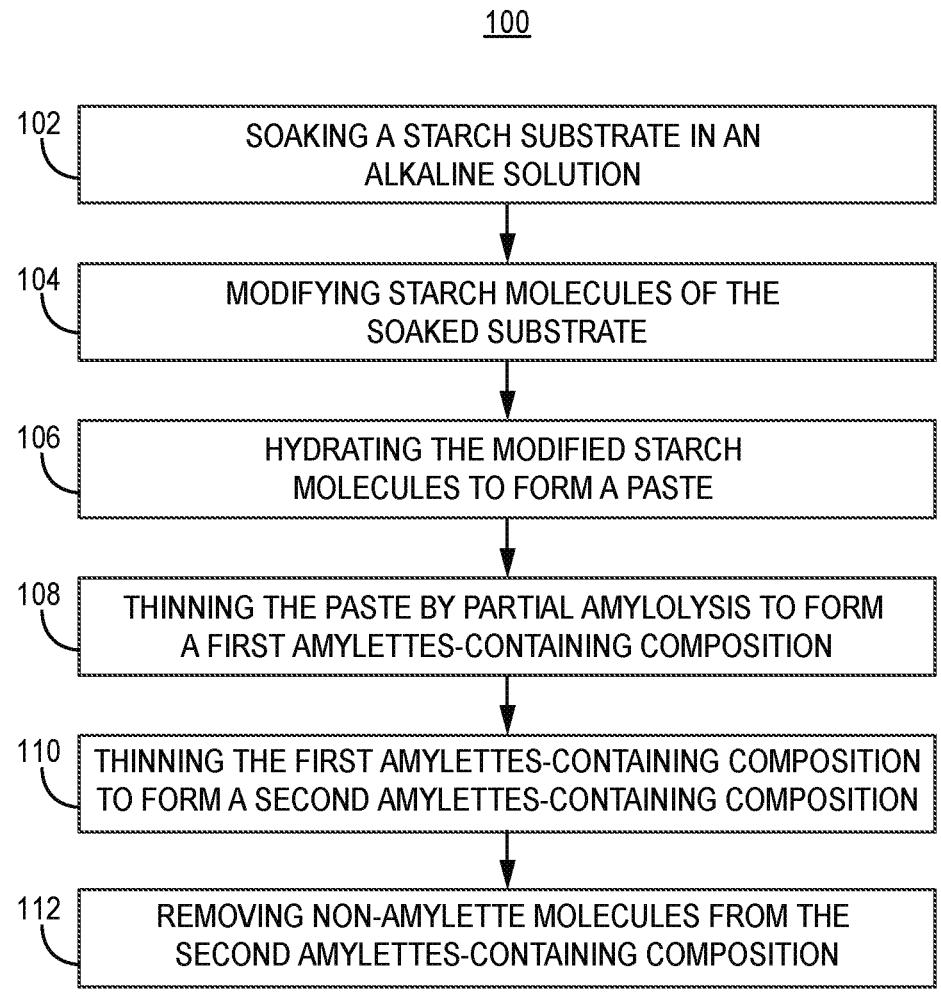
FIG. 1 describes materials and methods for preparing a clathrate-forming composition, according to one or more embodiments of the present disclosure.

Generally, embodiments of the present disclosure describe methods for preparing one or more clathrate-forming compositions from a starch-containing substrate and the clathrate-forming compositions so prepared. One or more of the embodiments describe preparing a starch-containing substrate for targeted enzymatic release of a plurality of linear glucomonomer chains of about 15 to about 100 D-glucopyranosyl residues linked by α-1,4 linkages. The linear glucomonomer chains are capable of accommodating a guest hydrophobic molecule within a single helix having 6-8 glucose units per turn, or accommodating a guest hydrophobic molecule between these helices, and thereby enhancing dispersion of the hydrophobic guest molecule in an aqueous composition. The manner of accommodation can be based on the structure of the guest (e.g., the size, presence of hydrophilic moieties, etc.) or the nature of the dispersion medium (e.g., the hydrophilic-hydrophobic balance (HLB) of the medium). In some cases, a plurality of amylettes can associate with a guest molecule (e.g., a bulky guest molecule) and thereby, shield hydrophobic moieties, improving the solubility or dispersibility of the guest molecule in water (or other aqueous medium). The dispersion can be a molecular dispersion of the guest molecule.

The clathrate-forming compositions of the present disclosure can be prepared using step-wise amylolysis of a modified starch substrate. Embodiments of the present disclosure can provide partially amylolyzed modified starch products that are flowable at temperatures within a range of 4-20° C. at a 20% w/v solids content and comprise one or more clathrate-forming molecules. In some cases, a clathrate-forming molecule which has been released, and optionally isolated from, a partially amylolyzed modified starch is a linear glucomonomer chain of about 15 to about 100 D-glucopyranosyl residues linked by α-1,4 linkages, or a chain of amylose having a degree of polymerization of at least 250. Isolating fractions of the clathrate-forming compositions facilitates further modification of target clathrate-forming molecules to enhance one or more properties such as dispersibility, stability, or complex formation. In some cases, the unmodified or modified clathrate-forming molecules can be combined to for tailored delivery formulations for specific guest molecules.

Definitions

The terms recited below have been defined as described below. All other terms and phrases in this disclosure shall be construed according to their ordinary meaning as understood by one of skill in the art.

The term "amylette" refers to a chain of about 15 to about 100 glucomonomers (i.e., D-glucopyranosyl residues) linked by α-(1→4) linear linkages derived from a modified starch. For example, an amylette can have a chain length of about 30 to about 90 linear α-(1→4) linked glucomonomers. Clathrate-forming compositions comprising amylettes are obtainable by physically, chemically and enzymatically modifying starch, using processes that control hydrolysis of the amylose (i.e., amylolysis) and/or amylopectin present in the starch. Amylettes can include amylodextrins and dextrins. Amylettes may include one or more esterified glucomonomers; however, in one or more embodiments, none of the glucomonomers of the amylettes are esterified. In some cases, amylettes include at least two types of esters: (1) one or more esters added prior to amylolysis (i.e., the starch modifying substituents) and (2) one or more esters added after amylolysis.

As used herein, "clathrate" refers to a host-guest complex or an inclusion compound.

A "clathrate-forming" composition or molecule of the present disclosure is capable of accommodating one or more guest molecules as a host of a host-guest complex or inclusion compound.

The term "flowable" used with respect to a 20% w/v solids composition formed by partial amylolysis of a modified starch substrate refers to a substantially liquid or slightly viscous composition, such as a weak gel. A flowable composition of the present disclosure has a dynamic viscosity of less than 2500+/−5% mPa·s at 20° C. within the temperature range of about 4 to about 20° C. as determined on a Rotary Viscometer (KUNHEWUHUA, model DNJ-8S) with #2 spindle at 0.3 rpm when the solids content of about 20% w/v.

The term "isolated" as used herein with respect to amylettes or long-chain amylose refers to molecules which have been separated from some or all of the other starch-derived products present in the starting material.

For the purposes of the present invention, the term "legume" refers to any plant belonging to the Cesalpiniacea, Mimosacea or Fabaceae families, with preference for plants belonging to the Fabaceae family, for instance pea, bean, lentil, alfalfa, clover, peanut, soybean and lupin. The term "pea" refers to seeded peas of the wild varieties and all the mutant varieties of pea, irrespective of the uses for which the variety is generally intended (human food, animal nutrition and/or other use). Exemplary pea varieties or cultivars include yellow pea, field pea, garden, green pea, smooth pea and wrinkled pea.

As used herein with respect to long chain amylose, "long chain" refers to amylose having a degree of polymerization (DP) of at least 250. In some cases, the long chain amylose has a DP 250-950.

As used herein, "poorly water soluble" refers to a molecule requiring more than 100 parts water to dissolve one part solute. A "water insoluble" molecule is a molecule requiring more than 10,000 parts water to dissolve one part solute.

As used herein, "modified starch" refers to starch that has been chemically altered from its native form to resist retrogradation, enzymatic hydrolysis, or a combination thereof, with preference for starch chemically altered by esterification.

As used herein, the term "molecular dispersion" refers to a composition including a dispersion medium in which a plurality of guest molecules are homogeneously distributed. A molecular dispersion can include guest molecules in the form of clathrates, such as inclusion complexes with amylette molecules or long chain amylose molecules.

As used herein, "restrained enzyme treatment" refers to enzymatic treatment under conditions that limit the activity of the enzyme to significantly less than optimum activity. A "restrained enzyme" exhibits no greater than 60% relative activity, where relative activity is the ratio between the activity of the enzyme under actual conditions and the activity of the enzyme under optimal conditions and therefore, can be expressed as a percentage. Enzyme activity can be defined in terms of the rate of substrate consumption and/or product formation for specific reaction conditions. Optimal conditions for an enzyme can be determined by direct testing or based on product literature.

As used herein, the term "wrapped" refers molecular encapsulation of a guest molecule in a cavity of an amylose helix, such as a V-type amylose helix.

As used herein, "wrapped molecular dispersion" refers to an aqueous suspension one or more guest molecules (or inclusion complexes) within at least partially retrograded amylose chains. Preferably, a wrapped molecular dispersion has an ordered structure that is more resistant to enzymatic digestion than gelatinized amylose (i.e., amylose with a disordered structure after processing or cooking).

Generally, methods for preparing clathrate-forming compositions from a starch-containing substrate include: (1) preparing the starch-containing substrate for release of target clathrate-forming molecules from the components of the substrate; (2) releasing the target clathrate-forming molecules from the components by amylolysis; and (3) isolating target clathrate-forming molecules from the products of amylolysis.

FIG. 1 describes method 100, an embodiment of the general method for preparing clathrate-forming compositions. The final products of method 100 include an isolated amylettes composition which is substantially free of long-chain amylose, amylopectin, and other non-amylette molecules released from the starch-containing substrate. In step 102, the method of preparing a clathrate-forming composition includes soaking a starch-containing substrate in an alkaline solution. During soaking ions of the solution can penetrate the substrate. Soaking the starch-containing substrate prepares the starch molecules within the substrate for subsequent modification. Soaking includes suspending the starch-containing substrate in an alkaline aqueous solution. The starch-containing substrate can be a substrate containing naturally-occurring starch molecules that are found in plants such as corn, potato, rice, wheat, legumes, etc., encompassing flour which contains other ingredients such as gluten, oil, fiber, etc., and raw starch granules.

The composition and structure of starch granules varies considerably between different plants, thus affecting the properties and functionality of starches from different crops. A suitable starch-containing substrate can be selected based on the amylose content, gelatinization temperature and/or the viscosity, texture and clarity of its paste. For example, a suitable starch can have one or more of the following characteristics: an amylose content greater than 25% and a gelatinization temperature that is less than 80° C. In some cases, a suitable starch can form a paste with medium to low viscosity, short texture, or low clarity. Preferably, the starch is extracted from a legume, or more preferably, extracted from a plant of the Fabaceae family. In some cases, the starch is a pea starch, such as a yellow pea starch, having one or more of the following properties: an amylose content of about 35%, a gelatinization temperature of about 65-75° C., a short texture and a low viscosity paste. In some cases, the starch can be a yellow pea starch such as the starch sold under the trade name Accu-Gel™ (Nutri-Pea Ltd, Manitoba, Canada). The starch may contain various constituents other than starch and proteins, such as fats, colloidal substances, fibers, and minerals, or the starch may be treated to substantially remove one or more of the proteins, fats, colloidal substances, and fibers. For example, pea flour can be filtered or agitated to remove chaff and proteinaceous materials in order to obtain granular starch.

The soaking solution can include water, such as tap water, distilled water, or pure water and is adjusted to have a pH greater than 10.5, such as a pH of about 11. A pH within the range of greater than 10.5 to 11 provides a higher concentration of ions for greater penetration of starch granules than a pH of 10.5 or lower. In some cases, the pH is adjusted within the range of 10.6-12, 10.7-11.8, 10.8-11.6 or 10.9-11.5. A suitable vessel for suspending and soaking the starch-containing substrate can be configured to monitor pH. The pH can be adjusted with a soluble base, such as an alkali metal hydroxide (e.g., sodium and potassium hydroxide), an alkaline earth metal base, such as calcium carbonate, or a quaternary onium, such as quaternary ammonium, sulfonium and phosphonium compounds. Preferably, the alkaline aqueous solution comprises sodium hydroxide as sodium ions can penetrate starch granules and facilitate uniform modification along the glucomonomer chains of the amylose as well as on interstitial glucomonomer chains between the 1,6 linkages of amylopectin molecules. In an exemplary embodiment of process 100, the starch-containing substrate is a legume starch, such as a starch extracted from *Pisum sativum*, and step 102 includes soaking in an alkaline aqueous solution including sufficient NaOH to provide a pH of 10.90-11.50.

In one or more embodiments of the present disclosure, the soaking vessel is also configured to monitor and control temperature. Soaking proceeds for a period of time sufficient for penetration of the starch granules and migration through the granule. The temperature can be controlled to reduce or avoid excessive alkaline degradation of the starch-containing substrate during the soaking period. For example, the starch-containing substrate can soak for greater than 6 hours to less than 30 hours, when the temperature is 25° C. or less without excessive alkaline degradation. In some cases, the starch-containing substrate can soak for about 12 hours at a temperature of about 15° C., or about 24 hours at a temperature of 4-10° C. In some cases, soaking includes mechanically agitating the suspension, such as, by stirring.

In step 104, the method of preparing a clathrate-forming composition includes modifying the soaked substrate. In some cases, the starch amylose and/or amylopectin molecules of the substrate are modified by converting some of the hydroxyl groups along the glucomonomer chains to esters. The modification provides at least two advantages for further processing of the starch molecules: (1) limiting irreversible retrogradation of amylose molecules released after hydration/hydrolysis of the starch, and (2) reducing susceptibility to amylolysis. Preferably, the placement of ester groups is substantially uniform along starch molecules, such as amylose chains and at least a portion of the amylopectin glucomonomer chains. The starch molecules can be modified to a desired degree of substitution (DS), i.e., the average number of hydroxyl groups replaced per glucose unit. The higher the DS, the greater the reduction in susceptibility to enzymatic hydrolysis. According to one or more embodiments of the present description, modifying starch molecules includes esterifying the starch to achieve a DS of at least 0.08 and up to about 0.15, such as about 0.10 to about 0.15, about 0.12 to about 0.15 or about 0.13 to about 0.15. The DS can be controlled by monitoring the consumption of esterification reagent, and replenishing reagent as necessary. The DS of the product can be verified by empirical methods such as titration, nuclear magnetic resonance (NMR), Fourier transform infrared spectroscopy (FT-IR) and headspace gas chromatography.

In some cases, modifying the soaked substrate includes placing acyl groups along amylose chains and at least a portion of the amylopectin glucomonomer chains. Accordingly, the esterification reagent can be an acylating agent, such as an acid anhydride, acid halide or an alkali metal salt of a carboxylic acid. For example, the acylating agent can be an acid anhydride such as acetic, propionic, octenyl succinic, phthalic, maleic, and succinic acid anhydrides, or a mixture of two or more of these acid anhydrides; an acid hydride such as acetyl chloride, butyric acid chloride, benzoyl chloride, propionic acid chloride, and stearyl chloride; or a alkali metal salts of carboxylic acids having between two and eight carbon acids.

The esterification reagent can be added to the reaction vessel slowly over a pre-determined period of time, in amounts sufficient to achieve a desired degree of substitution. The addition can be batchwise or via continuous feed. The degree of substitution or DS, which relates the average number of hydroxyl groups replaced by acyl groups or other derivatives per glucose unit. For example, using acetic acid anhydride as the acylating agent, the DS can be determined by monitoring the amount of sodium hydroxide used in the reaction during the acylation step to neutralize the acetic acid liberated during acetylation.

In step 106, the method of preparing a clathrate-forming composition includes hydrating the modified starch. In some cases, hydrating the modified starch requires diluting the modified starch composition to form a slurry with an acidic aqueous solution. The modified starch composition can be diluted by adding an amount of an aqueous medium, such as clean water, and then adjusting the pH within the range of about 4-6, such as about 5-6, or about 5.4. The amount of aqueous medium can be sufficient to dilute the solids content below about 40%, 35%, or 25% w/v, such as within a range of about 10-40%, about 15-35%, about 18-25%, or about 20% w/v solids content.

Hydrating the modified starch can include fully gelatinizing the starch by heating the modified starch composition. Heating physically disrupts the starch granules of the starch-containing substrate and opens the structure for subsequent enzyme action. Gelatinizing the starch can include heating a suspension of the modified starch until the starch exceeds its point of birefringence. Heating can be performed in a scraped surface steam jacketed kettle and at a temperature and duration sufficient for exposing amylose chains and unfolding amylopectin branches and clusters in the granules. Cooking temperature, water content, agitation, and cooking time can vary according to the concentration and source of starch, gelatinization temperature, stirring speed, water volume used, time, and evaluation methods, and whether the starch is pure, in the form of flour, or a formulated product. Generally, heating proceeds under continuous stirring above the starch gelatinization temperature in a water:starch ratio of 3:1 or more for more than 20 min. In some cases, the dilute suspension of modified starch is heated to at least about 65° C., such as at least 70° C., at least 80° C., or at least 90° C. and up to 200° C. In some cases, the suspension of modified starch is heated to a temperature within the range of about 50-175° C. or within a range of about 80-95° C. The fully hydrated starch is in the form of a very viscous paste. The paste is cooled in preparation for thinning by amylolysis.

In step 108, of the method of preparing a clathrate-forming composition includes a primary thinning step comprising thinning the hydrated paste by partial amylolysis using an endo-α-amylase enzyme. The endo-α-amylase cleaves glucomonomer chains and produces increasingly shorter amylose chains. Suitable endo-α-amylase enzymes include thermolabile enzymes exhibit relatively low thermostability, a relatively narrow range for optimum temperature, relatively low activity within the optimum temperature range, or a combination of two or more of these properties. Because a suitable endo-α-amylase enzyme can be thermally inactivated, step 108 includes cooling the hydrated paste to a temperature that is lower than the inactivation temperature of the selected endo-α-amylase. Preferably, the hydrated paste is cooled to a temperature that is also greater than the upper limit of the optimal temperature range of the enzyme. For process efficiency, the higher endpoint of the optimum temperature range is preferably greater than 35° C. More preferably, suitable enzymes are selected from endo-α-amylase enzymes with an optimum within the range of about 45-65° C., about 47-62° C., or about 50-60° C. A temperature higher than the upper limit of the optimum temperature range can be from 1-5° C. higher, such as about 2-4° C., or about 3-5° C. higher. In some cases, the hydrated paste is cooled to a temperature that is about 0.50, 0.75, 1.00, 1.25, 1.50, 1.75, 2.00, 2.25, 2.50, 2.75, 3.00, 3.25, 3.50, 3.75, 4.00, 4.25, 4.50, 4.75, or about 5.00° C. higher than the upper limit of the optimum temperature range of the alpha-amylase.

Control of the degree of hydrolysis is critical for preparing a composition enriched in clathrate-forming molecules including amylettes, with fewer over-hydrolyzed or under-hydrolyzed products than methods utilizing conditions for optimal enzymatic activity. A number of factors, including enzyme concentration, substrate concentration, pH, temperature, and the presence or absence of inhibitors or stabilizing ions can affect the degree of hydrolysis. In some cases, the degree of hydrolysis can be controlled by temperature, pH and shear. Preferably, the degree of hydrolysis can be controlled temperature alone. For example, temperature control over the degree of hydrolysis can be achieved by selection of an endo-α-amylase enzyme that can be inactivated by a relatively small increase in temperature. Preferably, the enzyme is one with a steep inactivation curve in response to slight changes to the composition of the cooled mass including the temperature, pH, amount of calcium present or a combination of two or more of these parameters. For example, a pH outside the optimal pH range can render an enzyme more sensitive to changes in temperature.

Endo-α-amylases are produced by several bacteria, fungi and genetically modified organisms. Suitable endo-α-amylase enzymes for thinning the paste include endo-α-amylase preparations of microbiological origin, such as those derived from organisms of the *Aspergillus* genus such as *A. niger, A. oryzae, A. fumigatus*, and *A. awamori*, including mutated strains, enzymes from genetically modified organisms, and chemically modified amylases therefrom. Preferably, the enzyme exhibits a steep temperature inactivation curve. For example, a food grade endo-α-amylases derived from *Aspergillus oryzae* can be active in a temperature range of 25° C. to 60° C. with optimum activity at 50° C., can begin to lose activity at prolonged periods of time above 60° C. and be thoroughly inactivated when held at greater than 70° C. for 30 minutes. Thus, the paste can be cooled to about 61-65° C. Use of an enzyme with a steep temperature inactivation curve reduces the use of pH adjusters or salts that may interfere with subsequent applications and enhances the energy efficiency to the process. Endo-α-amylases exhibiting substantially similar properties are commercially available under various trade names including FUNGAL AMYLASE L, sold by BIO-CAT microbials, having an optimum temperature range of 35-65° C., FUNGAMYL 800 L sold by Novozymes, having an optimum temperature of 55° C. Also suitable are some low temperature endo-α-amylases, such as the genetically modified bacterial enzyme sold under the trade name NATALASE (Novozyme), which has an application temperature range of about 10-60° C., and an optimal temperature of about 50° C.

After the paste temperature has been adjusted for the selected endo-α-amylase enzyme, step 108 includes adding the enzyme to the vessel. The endo-α-amylase can be added directly, or in a composition comprises a sufficient concentration of enzyme to provide the desired degree of amylolysis in view of the activity of the enzyme, the type of starch material, the degree of modification, and the amount of starch present. In some cases, the enzyme can be diluted in an aqueous solution. For example, an aqueous solution of about 10% w/v endo-α-amylase can be added to the vessel.

After the addition of the enzyme, thinning the starch paste includes maintaining or adjusting the vessel conditions to control of the degree of amylolysis. The vessel conditions are maintained or adjusted to restrain the activity of the enzyme so that it exhibits less than 60% relative activity. Enzymatic activity can be described in terms of relative activity or as % residual activity, where optimal conditions provide 100% activity. Amylase activity is generally defined as the quantity of enzyme which will breakdown, or dextrinize a predetermined amount of starch per unit time at a specific pH and temperature. Commercial sources provide enzyme activity. Residual activity refers to the enzyme activity that remains after exposure of the enzyme to negative effectors or to conditions that negatively impact enzyme structure/activity such as high temperature, pH extremes, etc., and for the purposes of the present disclosure, these terms can be used interchangeably. In some cases, the conditions ensure that the enzyme composition exhibits a relative activity of less than about 55%, 50%, 45%, 40%, 35%, 30%, 25%, 20%, or 15%, and at least 1% relative activity. As discussed above, the enzyme treatment is preferably controlled by maintaining the temperature within a range that restrains the activity to less than 60% but at least 1% activity. While activity can be restrained at temperatures lower than the optimal temperature range, higher temperatures can be preferable because the target molecules are energetically more active and present more binding sites for the enzyme. For example, in embodiments in which the primary enzyme treatment includes adding a fungal endo-α-amylase with an optimal temperature range of 45-60° C., the temperature can be maintained or adjusted to a temperature within the range of greater than 60° C. to about 68° C., about 62-65° C. or about 63-64° C. Thinning can include ensuring the temperature of the thinning composition is uniform by stirring. In some cases, the thinning composition is stirred at medium speed.

The duration of the thinning step depends on the amount of reactants, enzyme, the temperature of the reaction, and the desired degree of thinning. The duration can be adjusted based on the viscosity of the thinned product. For example, using a fungal endo-α-amylase with an optimal temperature range of 45-60° C., a sufficiently thinned product can have a dynamic viscosity of less than 400 mPa·s (spindle 2, at speeds of at least 3 rpm), under restrained temperature conditions (e.g., when measured at 60-68° C.).

Alternatively, the duration can be based on the relative concentration of very long chain amylose present in the thinned product, as indicated by an iodine complexation test. Starch can form an inclusion complex with polyiodide ions, which gives rise to a characteristic deep blue color. Amylose content of native starch is often determined colorimetrically from the iodine complexation. In amorphous domains, the conformation of amylose chains appears to be mainly in a single helical state or random coil. Dispersed amylose on retrogradation may form double-helical associations resulting in a gradual loss of its ability to form a blue complex with iodine. Relative chain length of amylose can also be determined by the amylose-iodine reaction as the color and λmax of the complexes change depending on amylose chain length and the helix cavity. The λmax of the complex increases with increasing amylose DP. Absorption peaks show a shift from blue to red as the chains are shortened by hydrolysis. Iodine does not form a stable complex with amylopectin (due to short length of the unit chains) and results in the formation of a purple color. Thus, in some cases, the reaction may be allowed to proceed until a point is reached which lies between that point where the reaction product gives a blue color with iodine to a point at which the reaction product gives a purple color with iodine.

Generally, the duration of the primary thinning enzyme treatment is at least 7 minutes and up to 20 minutes. For example, the duration of the primary thinning step can be about 8-18 minutes, about 9-16 minutes, or about 10-15 minutes, including about 10, 12, 14 or 15 minutes. The thinning step is terminated by inactivating the enzyme (e.g., by one or more of heating or pH adjustment, as discussed above). Preferably, the enzyme is inactivated by a change in temperature. The temperature required to inactivate the enzyme will depend on the enzyme selected. Generally, the reaction vessel is heated to a temperature higher that is at least 10° C. higher than the upper limit of the optimum temperature range for the enzyme, such as at least 15° C., at least 20° C., at least 25° C., at least 30° C. higher than the upper limit of the optimum temperature range. In some cases, the selected enzyme is thermally inactivated at 80-90° C. For example, heating can include applying steam to the vessel to achieve a temperature of 85° C.

The primary thinning step produces a first amylettes-containing composition, which can be characterized as semi-thinned gel, such as a thermoreversible gel, with variable melt points and curves. The thermoreversible gel can exhibit variable chilled gel strength. The first amylettes-containing composition is a relatively heterogeneous composition including at least some amylettes in the presence of non-amylette components of the starch granules. At this stage, the first amylettes-containing composition can be used to form a clathrate composition as described below, packaged for cool storage, or dried. In some cases, the first amylettes-containing composition is subjected to one or more of the processes described in step 112 below.

The yield of amylettes from the starch containing substrate can be enhanced by further thinning. In step 110, the method of preparing a clathrate-forming composition includes a second thinning step including thinning the first amylettes-containing composition by partial amylolysis using an endo-α-amylase enzyme. The first amylettes-containing composition is prepared for a restrained enzyme treatment by adjusting the temperature of the composition as necessary (i.e., heating or cooling) to a temperature that restrains the activity of the endo-α-amylase enzyme. As discussed for step 108, a suitable endo-α-amylase enzyme is selected from thermolabile enzymes and enzymes that exhibit relatively low thermostability. In some cases, the same enzyme is used for both the primary and secondary thinning steps.

Step 110 includes adjusting the temperature of the first amylettes-containing composition to a temperature below the inactivation temperature, but above than the upper limit of the optimal temperature range of the enzyme. Preferably, the composition temperature ensures the activity of the enzyme is restrained to a greater degree of activity than the degree of activity exhibited during step 108. In some cases, a temperature higher than the upper limit of the optimum temperature range can be from 4-10° C. higher, such as about 5-9° C., or about 6-8° C. higher. For example, the first amylettes-containing composition is adjusted to a temperature that is about 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, or about 9.00° C. higher than the upper limit of the optimum temperature range of the endo-α-amylase.

After the first amylettes-containing composition temperature has been adjusted for the selected enzyme, step 110 includes adding at least one aliquot of endo-α-amylase to the vessel. The endo-α-amylase can be added directly, or in a composition comprises a sufficient concentration of enzyme to provide the desired degree of amylolysis in view of the activity of the enzyme, the extent of amylolysis from the primary thinning, the degree of modification, and the amount of starch present. In some cases, the enzyme can be diluted in an aqueous solution. For example, an aqueous solution of about 10% w/v endo-α-amylase can be added to the vessel.

After the addition of the enzyme, thinning the first amylettes-containing composition includes maintaining or adjusting the vessel conditions to control of the degree of amylolysis. The vessel conditions are maintained or adjusted to restrain the activity of the enzyme so that it exhibits less than 40% relative activity. In some cases, the conditions ensure that the enzyme composition exhibits a relative activity of less than about 35%, 30%, 25%, 20%, 15%, 10%, 5%, 1%, or 0.5%, and at least 0.1% relative activity. Preferably, the enzyme treatment is controlled by maintaining the temperature within a range that restrains the activity to less than 40% but at least 0.1% activity. While activity can be restrained at temperatures lower than the optimal temperature range, higher temperatures can be preferable because the target molecules are energetically more active and present more binding sites for the enzyme. For example, in embodiments in which the primary enzyme treatment includes adding a fungal endo-α-amylase with an optimal temperature range of 45-60° C., the composition is heated or cooled to about 66-69° C., about 67-69° C., or about 68-69° C., for enhanced control over enzyme activity and faster inactivation, relative to the primary thinning step. The warmer temperature also results in increased movement of the glucomonomer chains and a more extended conformation of the chains, which enhances access of the enzyme to sites that, at lower temperatures, would be located in the interior of the molecule. As discussed above for primary thinning, secondary thinning can include ensuring the temperature of the thinning composition is uniform by stirring. In some cases, the thinning composition is stirred at medium speed.

Reaction conditions that include a temperature closer to the inactivation temperature results in gradual denaturation of the enzyme. Thus, step 110 can include adding a second aliquot of enzyme to replenish the enzyme activity to the desired restrained activity level. In some cases, before replenishment, the temperature is raised to inactivate any residual enzyme activity from the first aliquot. In this case, the temperature is raised only high enough to inactivate activate the residual activity so that the temperature can be readily lowered. For example, using FUNGAMYL 800L, the temperature is lowered to about 66-69° C., about 67-69° C., or about 68-69° C. before addition of the second aliquot of enzyme.

The duration of the secondary thinning step depends on the amount of reactants, enzyme, the temperature of the reaction, and the desired degree of thinning. The duration can be adjusted based on the viscosity of the thinned product and/or the relative concentration of long chain amylose present in the thinned product, as indicated by an iodine complexation test. The reaction may be allowed to proceed until a point is reached which lies between that point where the reaction product gives a purple color with iodine to a point at which the reaction product gives a red-purple color with iodine. Generally, the secondary thinning enzyme treatment has a duration of at least 7-15 minutes for each addition of enzyme. Thus, the total duration of secondary thinning can be within the range of 7-15 or 14-30.

The secondary thinning step is terminated by inactivating the enzyme (e.g., by one or more of heating or pH adjustment, as discussed above). Preferably, the enzyme is inactivated by a change in temperature. The temperature required to inactivate the enzyme will depend on the enzyme selected. Generally, the reaction vessel is heated to a temperature higher that is at least 10° C. higher than the upper limit of the optimum temperature range for the enzyme, such as at least 15° C., at least 20° C., at least 25° C., at least 30° C. higher than the upper limit of the optimum temperature range. In some cases, the selected enzyme is thermally inactivated at 80-90° C. For example, heating can include applying steam to the vessel to achieve a temperature of 90° C.

The secondary thinning step produces a second amylettes-containing composition, which can be characterized as thinned gel. The second amylettes-containing composition is a relatively heterogeneous composition including at least some amylettes and other components of the starch granules and/or plant cell of the starch source. At this stage, the second amylettes-containing composition can be used to form a clathrate composition as described below, packaged for cool storage, or dried.

In step 112, the method of preparing a clathrate-forming composition includes removing non-amylette molecules from the second amylettes-containing composition. Removing non-amylette molecules includes one or more processes selected from the group consisting of: degrading amylopectin, degrading cell wall polysaccharides, separating stabilized long-chain amylose molecules, converting amylopectin or amylose remnants to glucose, removing glucose, converting glucose to gluconic acid, and removing gluconic acid. Two or more of these processes can be performed together, at the same time, and in the same reaction medium, or each process can be performed separately (e.g., sequentially). The processes can be performed in any order. In some cases, one or more of these processes can be performed on the first amylettes-containing composition. After any of these processes or combination thereof, the resulting amylettes-containing composition can be used to form a clathrate composition as described below, packaged for cool storage, or dried.

A process of degrading amylopectin can include debranching the amylopectin component of the modified starch-containing substrate. The process can include treating the second amylettes-containing composition with a debranching enzyme, i.e. an enzyme capable of hydrolyzing the 1,6-glucosidic bond of amylopectin. Examples of useful enzymes include pullulanases derived from bacteria of the genus *Aerobacter* and isoamylases derived from bacteria of the genus *Pseudomonas*, and limit dextrinases. The debranching enzyme may be in solution during debranching. The optimum concentration of enzyme and substrate in the debranching medium will, in general, depend upon the level of activity of the enzyme which, in turn, will vary depending upon the enzyme source, enzyme supplier and the concentration of the enzyme in commercial batches. The debranching can be allowed to proceed until the desired degree of debranching has been obtained. Preferably, the degree of debranching is sufficient to convert more than about 80% of the amylopectin to short chain amylose and, more preferably, at least about 90% of the amylopectin. In preferred embodiments, essentially all of the amylopectin is converted to short chain amylose. After the desired degree of debranching is obtained, debranching enzyme in solution is deactivated, e.g. by heating to denature the enzyme.

A process of degrading cell wall polysaccharides can include hydrolyzing the polysaccharides by treating the second amylettes-containing composition with one or more carbohydrases capable of hydrolyzing polysaccharides such as pectin and/or hemicellulose. Examples of useful enzymes include arabanase, cellulase, β-glycanase, hemicellulase, and xylanase. The one or more carbohydrases may be in solution during hydrolysis. The optimum concentration of enzyme and substrate in the hydrolysis medium will depend upon the level of activity of the enzyme, as discussed above. The reaction can be allowed to proceed until the desired degree of hydrolysis has been obtained. After the desired degree of hydrolysis is obtained, debranching enzyme in solution is deactivated, e.g. by heating to denature the enzyme.

Preferably, the second amylettes-containing composition is treated with a combination of one or more debranching enzymes and one or more cell wall polysaccharide degrading enzymes simultaneously. For example, pullulanase and one or more carbohydrases can be used simultaneously. Alternatively, as described in Example 3 below, the amylettes-containing composition is treated with two debranching enzymes (e.g., pullulanase and dextrinase) and the one or more carbohydrases at the same time.

A process for removing amylose or amylopectin remnants can include treating the second amylettes-containing composition with a glucoamylase enzyme to convert the remnants to glucose. Preferably, to protect the amylettes (e.g., avoid over-hydrolysis), the reaction conditions are controlled to restrain the enzyme activity. For example, the reaction conditions are maintained or adjusted to restrain the activity of the glucoamylase so that it exhibits less than 90% relative activity. In some cases, the conditions ensure that the enzyme composition exhibits a relative activity of less than about 85%, 80%, 75%, 70%, 50%, 40%, 30%, 20%, or 15%, and at least 10% activity. The enzyme activity can be controlled by maintaining the reaction temperature within a range that restrains the activity to less than 90% but at least 15% activity. While activity can be restrained at temperatures lower than the optimal temperature range, higher temperatures can be preferable for energy efficiency and rapid thermal inactivation. The enzyme treatment can be controlled using a combination of sub-optimal temperature and sub-optimal pH as described in Example 4, below and FIGS. 10B-C. The optimum concentration of enzyme and substrate in the reaction medium will depend upon the level of activity of the enzyme. Preferably, the reaction converts substantially all the amylopectin or amylose remnants to glucose, after which the glucoamylase enzyme is deactivated, e.g. by heating to denature the enzyme.

Figure 14:
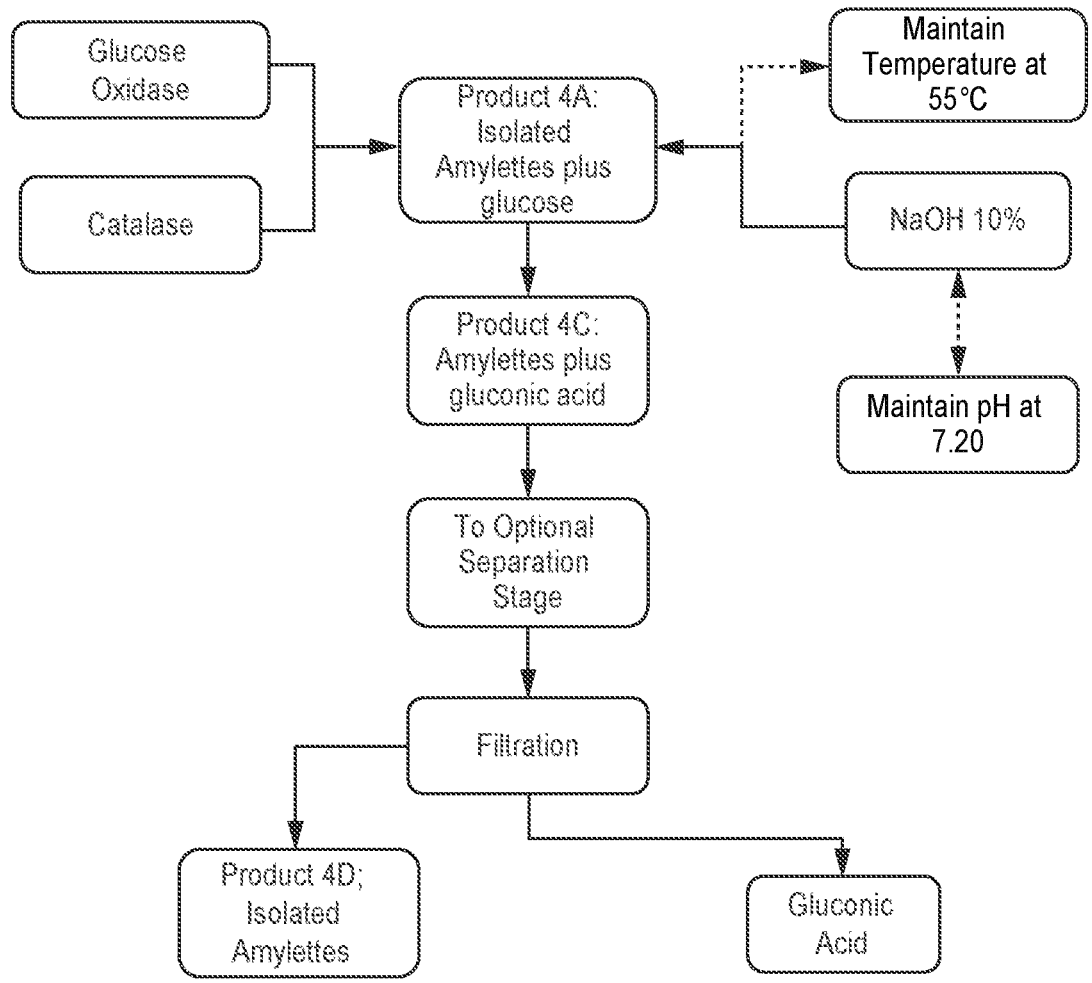
FIG. 14 is a flowchart describing materials and methods for preparing a sixth clathrate-forming composition, comprising isolated amylettes, referred to as "Amylettes Product 4D", according to one or more embodiments of the present disclosure.

A process for removing the glucose can be performed after glucoamylase treatment. Removing glucose can include enzymatically converting the glucose to gluconic acid. For example, the glucoamylase-treated composition can be treated with a combination of glucose oxidase and catalase enzymes, as described in FIG. 14. Preferably, at least 85% of the glucose is converted and more preferably, complete conversion occurs (at least 99% of the glucose is converted). During the conversion, alkali solutions (e.g., sodium hydroxide) can be added to neutralize the gluconic acid produced. Optionally, air, enriched air, or oxygen can be supplied for the conversion of glucose into gluconic acid. In some cases, step 212 further includes separating the gluconic acid from amylettes (e.g., by filtration).

A process of separating stabilized long-chain amylose from the second amylettes-containing can be advantageous because the stabilized long-chain amylose can utilized as a clathrate-forming molecule. Separating can include chilling the composition to precipitate amylose chains having a degree of polymerization of at least 250, and removing the precipitated amylose molecules from the suspension (e.g., by filtration or centrifugation). The stabilized long-chain amylose can be separated from the second amylettes-containing composition at different stages of step 212. After separation the stabilized long-chain amylose can be cooled and stored. In some cases, the stabilized long-chain amylose can be used to form wrapped molecular dispersions (e.g., as described in FIGS. 2A-C and 13). The stabilized long-chain amylose can be treated to restore its tendency to retrograde, as discussed in further detail below.

The present disclosure further describes methods for preparing amphiphilic clathrate-forming compositions comprising esterified amylettes. Amylettes produced by one or more of the methods described above are capable of adopting a helical conformation in water or in the presence of a hydrophobic guest molecule. The amylette helix exhibits a hydrophilic outer surface comprising hydroxyl groups and a hydrophobic inner cavity. For at least a portion of amylettes, the hydrophobic inner cavity includes one or more substituents derived from the modified starch starting material (e.g., acetyl groups). While not wishing to be bound by theory, one or more amylettes prepared by the processes described above may be released from portions of amylose (or amylopectin) between substituents. A lipid rich outer surface may improve the cellular targeting relative to amylettes that have not been esterified for improved delivery of a guest molecule. In addition, enhanced lipophilicity can improve the ability of the amylettes to complex with hydrophobic agents with lipophilic moieties and/or improve dispersibility of the amylette or a clathrate formed therefrom in both polar and non-polar solvents, such as water and vegetable oil, respectively.

Accordingly, embodiments of the present disclosure include a method of esterifying amylettes to enhance the relative lipophilicity of the molecule. An amylettes molecule may be partially or completely esterified. Preferably, amylettes are esterified with a fatty acid lipid donor. The degree of substitution (DS) can be 1.0 to 3.0 fatty acids per glucose unit. The DS can be selected to provide a specific hydrophile-lipophile balance (HLB) known to be useful for stabilizing dispersions of target guest molecules.

The fatty acid lipid donor can be selected from saturated and unsaturated fatty acids, include straight chain and branched fatty acids. For example, the fatty acid can be a single saturated or unsaturated straight chain fatty acid having up to 30 carbon atoms, a single saturated or unsaturated branched fatty acid each having 4 to 26 carbon atoms, or a combination thereof. In some cases, a straight chain saturated fatty acid, such as one with 8 to 22 carbon atoms is used (e.g., caprylic acid, capric acid, lauric acid, myristic acid, palmitic acid, stearic acid, arachic acid, behenic acid, or a combination thereof). In some cases, a saturated branched fatty acid, such as one with 4 to 26 carbon atoms is used (e.g., isobutyric acid, isovaleric acid, 2-ethylbutyric acid, ethylmethylacetic acid, isoheptanoic acid, 2-ethylhexanoic acid, isononanoic acid, isodecanoic acid, isotridecanoic acid, isomyristic acid, isopalmitic acid, isostearic acid, isoarachic acid, isohexacosanoic acid, or a combination thereof). In some cases, an unsaturated fatty acid is used, such as one with 6 to 30 carbon atoms (e.g., cis-4-decenoic (obtusilic) acid, 9-decenoic (caproleic) acid, cis-4-dodecenoic (linderic) acid, cis-4-tetradecenoic (tsuzuic) acid, cis-5-tetradecenoic (physeteric) acid, cis-9-tetradecenoic (myristoleic) acid, cis-6-hexadecenoic acid, cis-9-hexadecenoic (palmitoleic) acid, cis-9-octadecenoic (oleic) acid, trans-9-octadecenoic (elaidic) acid, cis-11-octadecenoic (asclepinic) acid, cis-11-eicosenoic (gondoleic) acid, cis-17-hexacosenoic (ximenic) acid, cis-21-triacontenoic (lumequenic) acid or a combination thereof). In some cases, a polyene unsaturated fatty acid is used, such as sorbic acid, linoleic acid, hiragoic acid, punicic acid, linolenic acid, γ-linolenic acid, moroctic acid, stearidonic acid, arachidonic acid, EPA, DHA, stearolic acid, or combinations thereof. The sources of the fatty acid lipid donor include natural fats and oils which have a high concentration of these fatty acids, e.g. soybean oil, olive oil, cottonseed oil, corn oil, tallow and lard. Preferably, the fatty acid lipid donor is stearic acid, oleic acid, palmitic acid, lauric acid, linoleic acid, or hexanoic acid (AKA caproic acid).

According to one or more embodiments of the present disclosure, the ester bond formation between a fatty acid lipid donor and a hydroxyl group of an amylette is catalyzed by a lipase enzyme. Thus, the present disclosure also includes a process for preparing a fatty acid ester comprising reacting an amylettes with at least one fatty acid in the presence of a lipase in an aqueous medium. Any commercial lipase preparation may be used including one of the various microbial lipase preparations obtained from genus *Aspergillus, Pseudomonas, Enterobacterium, Chromobacterium, Geotrichum, Penicillium, Mucor, Candida,* and *Rhizopus*. In some cases, the lipase preparation is obtained from *Candida cylindracea*. For example, the lipase can be the *C. cylindracea* preparation from Enzyme Development Corp., sold under the trade name ENZECO® LIPASE CONCENTRATE.

The esterification reaction may be carried out by adding the enzyme to an aqueous composition comprising the substrates (amylettes and fatty acid lipid donor) and incubating the mixture at the optimal pH range for the enzyme. Generally, the pH is between 4 and 9, preferably between 5 and 8. In some cases, the substrates are present in the form of a molecular dispersion before addition. Without being bound by theory, it is believed that the proximity of the substrates within a molecular dispersion increases the reaction yield relative to less complex mixtures (e.g., emulsions). The molar ratio of amylettes to fatty acid may vary from 1:10 to 10:1. Forming the molecular dispersion includes combining an aqueous amylettes-containing composition and a fatty acid lipid donor, heating the combination to melt the lipid donor fatty acid and mixing the combination under high shear. The aqueous amylettes-containing composition can include about 20% w/v solids. The molecular dispersion is then cooled to a temperature appropriate for the lipase enzyme. The temperature may range between about 20° C. and about 60° C., between about 30° C. and about 50° C., or between about 40° C. and about 45° C.

The amount of lipase enzyme relative to the substrates can vary with the activity of the lipase preparation. In some cases, the lipase can be present at about 0.1-10% by weight relative to the weight of the substrate solids. The esterification reaction is reversible and the incubation is terminated when the reaction reaches an equilibrium. The amylettes fatty acid ester containing mixture is heated and held at elevated temperature until the lipase is inactivated. The amylette fatty acid esters may be recovered and purified using known methods.

Embodiments of the present disclosure further describe clathrates formed using any of the amylettes-containing compositions described above. In some cases, clathrates are formed from an amylettes-containing composition from which substantially all non-amylette molecules have been removed (i.e., isolated amylettes compositions). The amount of hydrophobic guest used to prepare a complex, relative to the amount of amylettes may vary from a weight ratio of about 1:10 to 1:2. In some cases, the hydrophobic guest is solubilized and/or melted before dispersion in a drop-wise manner into an aqueous amylettes-containing composition, as described in Example 7, below. The hydrophobic guest can be resveratrol, vitamin E, vitamin D, quercetin, diindolylmethane, coenzyme Q10, or cannabidiol (CBD). Solid complexes can be prepared by removing the water, as by freeze drying, spray drying, or other suitable manner for removing the water. For example, water can be removed by heating the composition when non-volatile guest molecules are complexed.

Additional embodiments of the present disclosure include resistant clathrate compositions, formed by dispersing a hydrophobic guest molecule in an aqueous composition of an unmodified long-chain amylose molecules. The dispersion can be formed under shear to produce a molecular dispersion. The unmodified long-chain amylose can wrap around the hydrophobic guest molecule. Digestive enzymes do not recognize retrograded starch structure. Thus, this property can be utilized to provide clathrate composition that are stable in the upper digestive system (including the mouth, esophagus, stomach and small intestine) of healthy individuals.

Advantageously, methods of the present disclosure can use separated stabilized long chain amylose to prepare unmodified amylose for resistant clathrates. After separation from one or more of the clathrate-forming composition described above, stabilized long-chain amylose can be de-esterified to restore the tendency of the amylose molecule to form retrograde crystallization products. For example, acetyl groups substituted on the amylose during the modification step can removed by acid or base catalyzed hydrolysis. See, for example, Example 6 below. After hydrolysis the destabilized long chain amylose can be collected and stored for use. Resistant clathrate compositions can also be formed by dispersing a clathrate formed with an amylettes-containing composition as discussed above in an aqueous composition of the de-esterified long-chain amylose with shear to form a molecular dispersion, and allowing the de-esterified long-chain amylose to wrap around the clathrate, as exemplified in Example 7 below, for example.

Embodiments of the present disclosure further describe kits for forming a molecular dispersion and/or clathrate with a hydrophobic guest molecule. For example, a kit can include a first container comprising a clathrate-forming composition comprising amylettes, as described above, and instructions for preparing a molecular dispersion or clathrate with a genus of hydrophobic guest molecules or a specific hydrophobic guest molecule (e.g., cannabidiol). The clathrate-forming composition can be supplied in the form of a solid or an aqueous composition. If provided in a solid form, the kit can include a dispersion medium suitable for reconstituting the composition and for obtaining the molecular dispersion or clathrate. In some cases, the clathrate-forming composition can be an amphiphilic clathrate-forming composition comprising esterified amylettes, such as a fatty-acid esterified amylettes composition (e.g., a stearic acid esterified amylette composition). The container can be any suitable container for the volume and type of material to be packaged.

A hydrophobic guest molecule can be included with the kit or be supplied by the end user. In some cases, one or more hydrophobic guest molecules are supplied. The kit can include separately packaged solvents and/or antioxidants for use preparing the hydrophobic active for dispersion in the clathrate-forming composition. The guest molecule can resveratrol, vitamin E, vitamin D, quercetin, diindolylmethane, coenzyme Q10, or cannabidiol, for example. Volatile, oxidation sensitive, or photosensitive guest molecules can be packaged in specialized containers to prevent loss or degradation of the guest molecule.

In one or more embodiments, the kit can include a composition comprising a plurality of amylose chains having a degree of polymerization of at least 250, with instructions for wrapping the clathrated hydrophobic guest molecule in the amylose chains. These long chain amylose molecules can be included in a separate container, and in the form of an aqueous suspension or dried solid. The plurality of amylose chains can be stabilized (as-modified during by the modifying step described above) or de-stabilized (with the modification removed).

In some cases, a kit can include instructions for drying the molecular dispersion and/or formulating the dried complexes or compounds in a delivery vehicle for a desired route of administration.

Figure 2A:
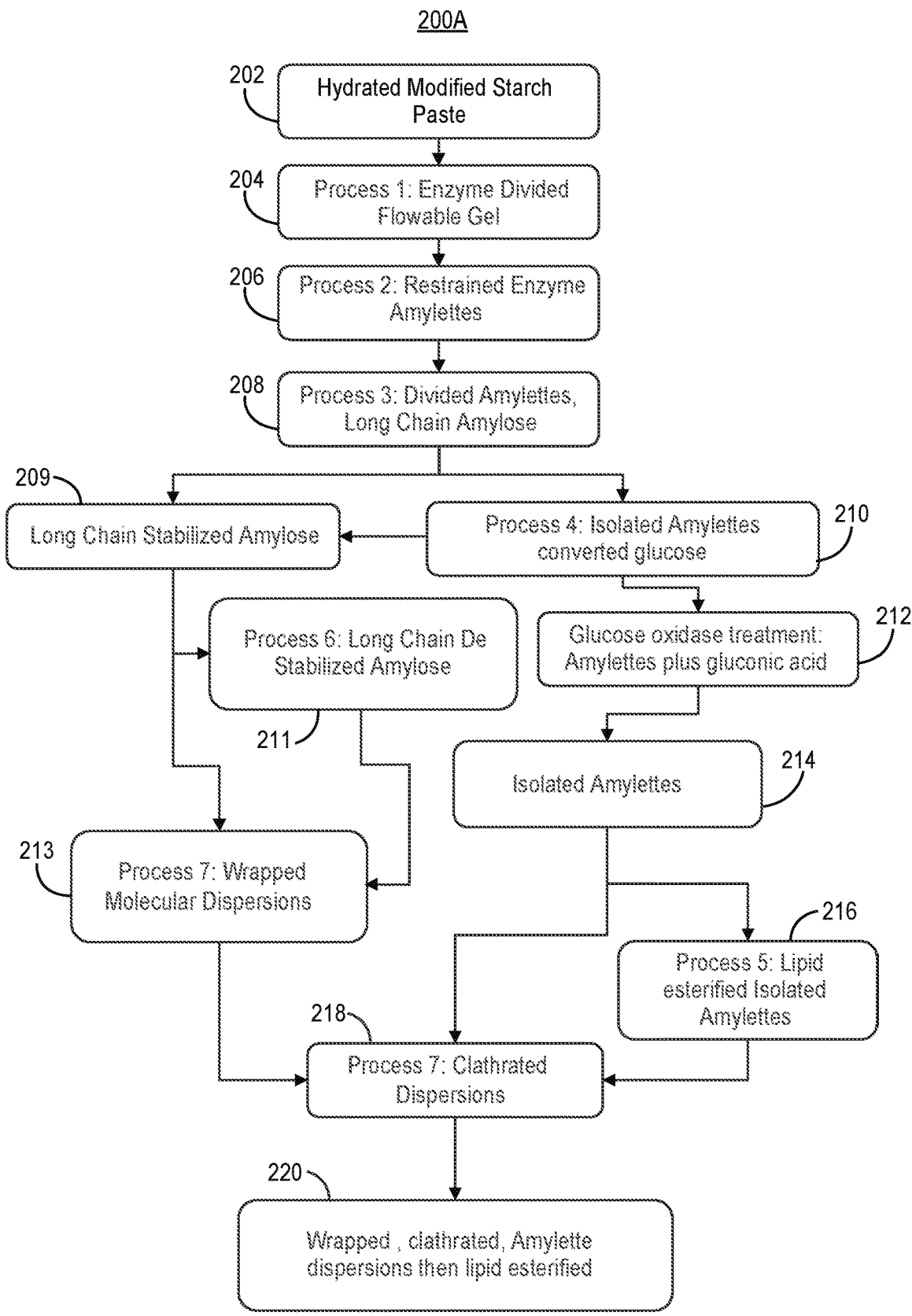
FIGS. 2A-C provide flowcharts describing the materials and methods for preparing clathrate-forming compositions and clathrates formed therefrom, according to one or more embodiments of the present disclosure. (A) describes various compositions derived from a hydrated modified starch paste; (B) describes an alternative process for producing clathrate-forming compositions and clathrates formed therefrom, using an amylase-treated modified starch gel according to a prior art method (U.S. Pat. No. 7,550,270); (C) describes an alternative process describes an alternative process for producing clathrate-forming compositions and clathrates formed therefrom using a partially amylolyzed modified starch composition.
Figure 2B:
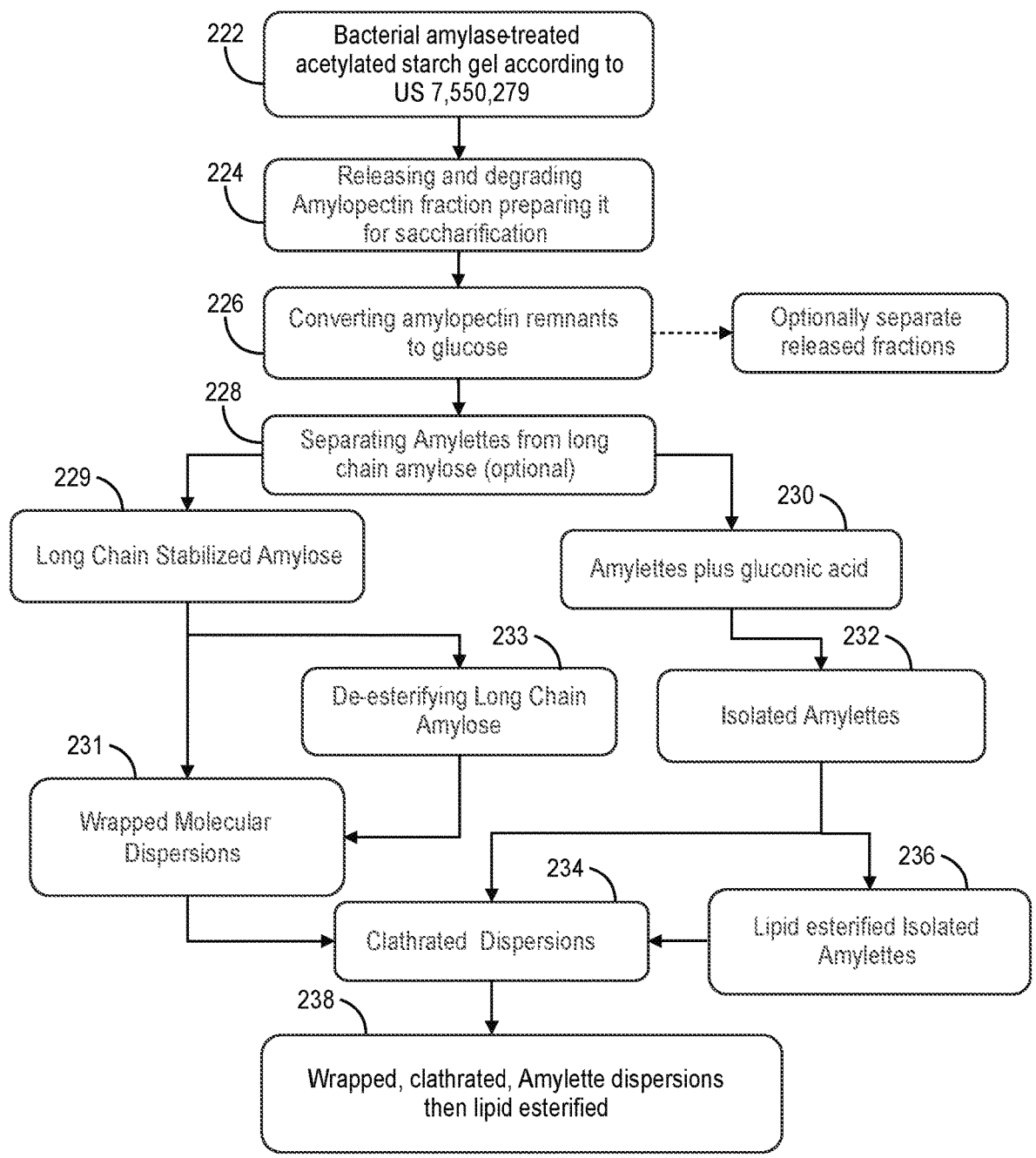
Figure 2C:
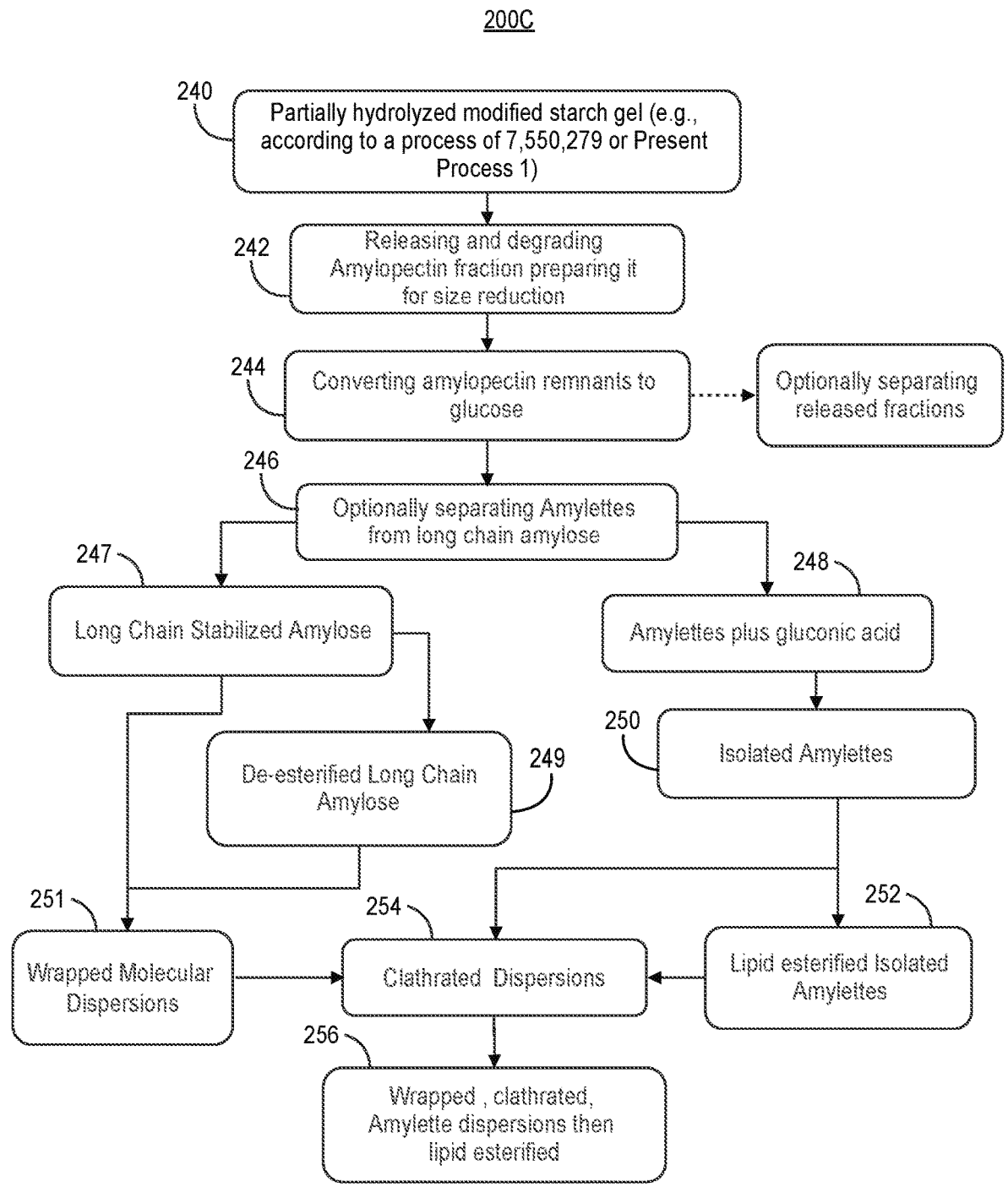

FIGS. 2A-C describe alternative embodiments of method 100, and compositions obtainable thereby. FIG. 2A describes a general scheme for step-wise liberation and isolation of amylettes from the other components of a modified starch material, and the use of the prepared amylettes compositions as molecular dispersion host compositions for formulation and delivery of one or more guest molecules. Processes identified by a number (e.g., "Process 1") below refer to exemplified embodiments described in the Example section.

In FIG. 2A, a hydrated modified starch paste 202, such as a paste prepared according to steps 102-106, can be subjected to "Process 1", including a first enzymatic thinning as described in step 108, to prepare a flowable "Enzyme Divided Gel" 204. Enzyme Divided Gel 204 includes clathrate-forming amylettes. Enzyme divided gel 204 can be refined using the materials and methods of "Process 2", including a second enzymatic thinning as described for step 110. Process 2 can be used to prepare "Restrained Enzyme Amylettes" 206 characterized by a lower viscosity than the precursor gel 204. The restrained enzyme amylettes 206 of Process 2 can be further refined using the materials and methods described in step 112 (e.g., one or more of Processes 3-5). For example, "Process 3" can include removing long-chain amylose from the restrained enzyme amylettes 206, and thereby prepare at least two compositions: (1) a "Divided Amylettes" composition 208, which is substantially free of long chain amylose molecules; and (2) a "Long Chain Stabilized Amylose" composition 209, which composition may comprise esterified amylose where the stabilizing modification is an esterified starch. The divided amylettes composition 208 can be further refined using "Process 4", including removing amylopectin and cell wall polysaccharides, and thereby prepare an "Isolated Amylettes converted glucose" composition 210, which is substantially free of long chain amylose, amylopectin, and cell wall components. The glucose in product 210 can be removed by a glucose oxidase treatment, and thereby prepare an "Amylettes" composition 212 that is substantially free of glucose, but which includes gluconic acid. The gluconic acid in product 212 can be removed by filtration or other separation technique, thereby prepare an "Isolated Amylettes" composition 214 that is substantially free of long chain amylose, amylopectin, glucose, gluconic acid and cell wall components. The isolated amylettes 214 can be used to prepare clathrated dispersions 218 of one or more guest molecules using "Process 7". The isolated amylettes can be modified by lipid transesterification to prepare a "Lipid esterified Isolated Amylettes" composition 216. The lipid esterified amylettes 216 can also be used to prepare "clathrated dispersions" 218 with one or more guest molecules using Process 7. The long chain stabilized amylose 209 isolated by Process 3 can be de-stabilized using "Process 6". In some cases, Process 6 can be used to prepare de-esterified amylose 211, which exhibits increased instability relative to the esterified amylose and a restored retrogradation tendency. One or both of the long chain stabilized amylose composition 209 and de-stabilized amylose composition 211 can be used to prepare wrapped molecular dispersions 213 with one or more guest molecules using Process 7. The wrapped molecular dispersions 213 can be combined with the clathrated dispersions 218 to prepare a wrapped, clathrated dispersion including lipid esterified amylettes 220 for formulation and/or delivery of the one or more guest molecules.

The properties of the clathrate-containing compositions can be tuned by selecting a specific type of starting material. FIG. 2B describes an alternative scheme 200B for liberating and isolating amylettes present in a bacterial amylase-treated acetylated starch gel, as the "ButterGel" described in U.S. Pat. No. 7,550,279, for isolating and de-acylating long chain amylose, and further describes using the starch-derived products to form various host:guest delivery compositions. This starting material is structurally distinguishable from the starting material in FIG. 2A (e.g., different placement of substituents on the starch components during modification results in different degree of steric hindrances for the bacterial enzyme which leads to different products released by amylolysis), and therefore, each subsequent process lead to further differences in the properties of the clathrate-forming compositions (e.g., melting profile, stability, and affinity for different guest molecules). For example, the gel of the '279 patent produces a compositions with a firm to hard gel strength upon cooling, which are intended to contribute to the structure and texture of the final food product. In FIG. 2B, a bacterial amylase-treated acetylated starch gel 222 can be subjected to step 224 including releasing and degrading the amylopectin fraction and the remnants of degraded amylopectin can be converted to glucose in step 226, or optionally separated. The substantially amylopectin free gel can be further processed in optional step 228 by separating the amylettes and glucose from the long-chain acetylated amylose. The resulting amylettes and glucose product can be treated by converting the glucose to gluconic acid in step 230, and the amylettes isolated in step 232. The isolated amylettes can be used to form clathrated dispersions of one or more guest molecules in step 234, or a lipid esterified in step 236. The lipid esterified amylettes can be used to form clathrated dispersions including one or more guest molecules in step 234. The long chain acetylated amylose product 229 can be used to form wrapped molecular dispersions of one or more guest molecules in step 231 or de-esterified in step 233. The de-esterified long chain amylose can be used to form wrapped molecular dispersions of one or more guest molecules in step 231. The wrapped molecular dispersions can be combined with one or more clathrated dispersions formed in step 234 to provide wrapped, clathrated dispersions which may include lipid esterified amylettes in step 238.

FIG. 2C describes an alternative scheme 200C for liberating and isolating amylettes present in any partially hydrolyzed modified starch product. In FIG. 2C, a partially hydrolyzed modified starch material 240 can be subjected to step 242 for releasing and degrading the amylopectin fraction. The remnants of the degraded amylopectin can be converted to glucose in step 244 or optionally separated. The substantially amylopectin free gel can be further processed in optional step 246 by separating the amylettes and glucose from the long-chain acetylated amylose. The glucose can be converted to gluconic acid in step 248, and the amylettes isolated in step 250. The isolated amylettes can be used to form clathrated dispersions of one or more guest molecules in step 252, or lipid esterified in step 254. The lipid esterified amylettes can be used to form clathrated dispersions of one or more guest molecules in step 256. The long chain acetylated amylose product 247 can be used to form wrapped molecular dispersions of one or more guest molecules in step 251 or it can be de-esterified in step 249. The de-esterified long chain amylose can be used to form wrapped molecular dispersions of one or more guest molecules in step 251. The wrapped molecular dispersions can be combined with one or more clathrated dispersions of step 254 in step 256, to form wrapped, clathrated dispersions which may include lipid esterified amylettes.

The methods and materials of the present invention will be further described in the following examples. These examples are intended to illustrate the above invention and should not be construed as to narrow its scope. One skilled in the art will readily recognize that the Examiners suggest many other ways in which the invention could be practiced. It should be understood that numerous variations and modifications may be made while remaining within the scope of the invention.

EXAMPLES

Example 1: Preparation of Amylettes Product 1 from Granular Starch

Uniform Modification of Starch and Initial Chain Shortening—Amylettes Product 1

Figure 3A:
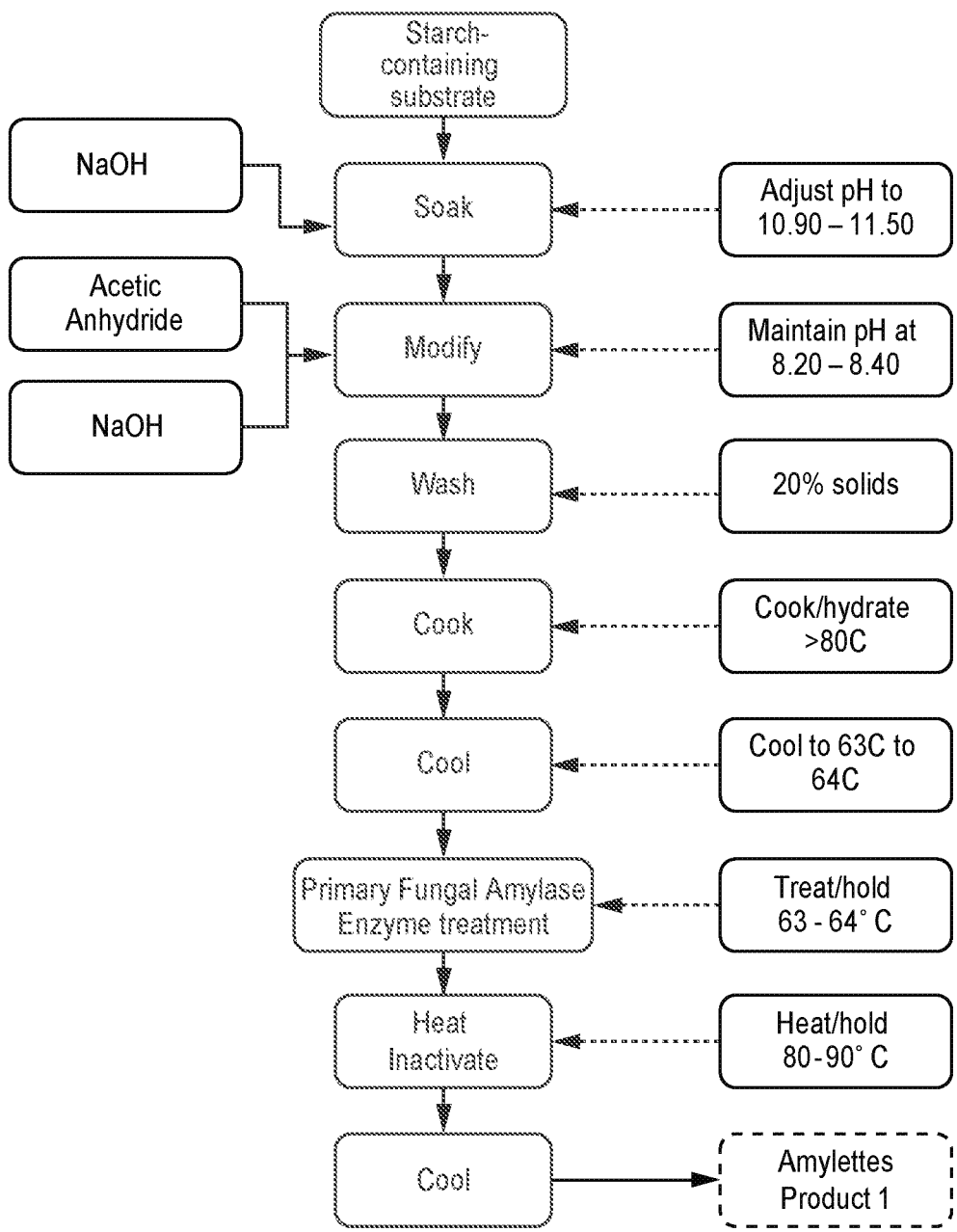
FIGS. 3A-B describe materials and methods for preparing a first clathrate-forming composition, referred to as "Amylettes Product 1", according to one or more embodiments of the present disclosure. (A) is a flowchart showing a production scheme for uniform modification of starch and initial chain shortening; (B) is a graph showing the effect of temperature on the relative activity of the fungal amylase sold under the tradename FUNGAMYL 800 L by Novozymes.

The following example describes an embodiment of Process 1, shown in FIG. 3A, with a legume starch as the starch-containing substrate.

Approximately 1372.1 kg (3025 lb) legume starch (Accu-Gel™ native granular pea starch, commercially available from Nutri-Pea Ltd.) was slurried in approximately 2,082 L (550 gal) of water in a reaction vessel with a stirrer. The pH was adjusted to 11 with NaOH (approximately 1.8 kg (4 lb)). The slurried starch was soaked in the alkaline solution for 12 hours at 15° C. while stirring. After soaking period, approximately 124.7 kg (275 lb) of acetic anhydride was added to the mixture over a 3 hour period while simultaneously adding 10% w/v sodium hydroxide solution at a rate sufficient to maintain the pH of approximately 8.3, to modify the legume starch. Additional acetic anhydride (approximately 4.5 kg (10 lb)) was added to the mixture to achieve a final pH of 5.7. Approximately 2460.5 L (650 gal) water was added to dilute the mixture and the mixture was desalinated by centrifugation. The solids content of the centrifuge feed was 21.6%. The supernatant was decanted. The resulting sediment cake weighed approximately 3374.7 kg (7,440 lb) with a solids content of 37.0%. The sediment cake was washed and diluted to provide a cooker feed with a target solids content of 20.0%. The total cooker feed was approximately 6243.2 kg (13,764 lb). Approximately 2868.5 kg (6,324 lb) wash water was added.

Figure 3B:
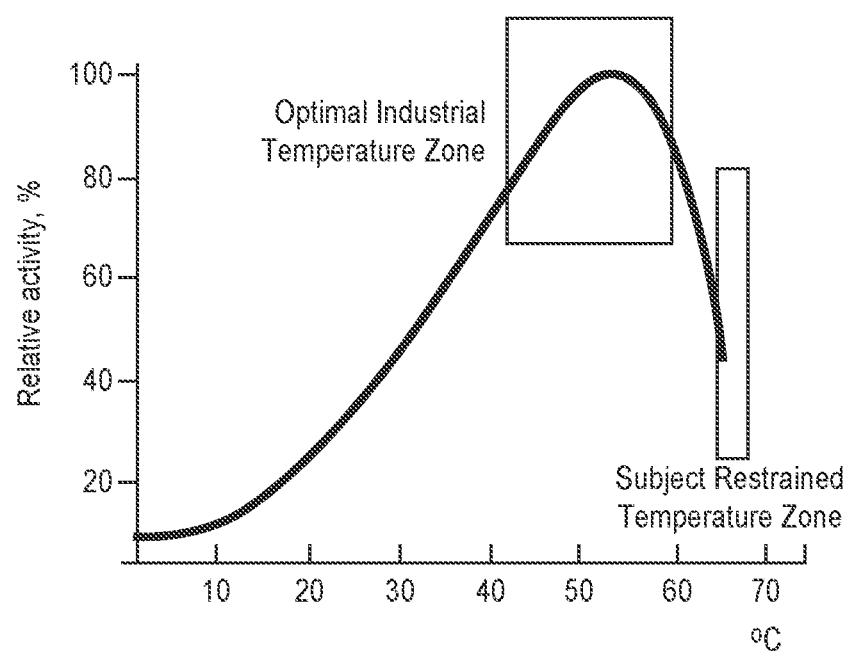

A portion of the modified legume starch (approximately 1040.5 kg (2294 lb)) was added to a double action scraped surface steam jacketed kettle and hydrated at 80° C. The hydrated starch mass was cooled to 63° C. and 13 g FUNGAMYL 800, a fungal alpha-amylase, commercially available from Novozyme was added. A first sample of the mixture was stirred at medium speed for 10 minutes ("Amylettes Product 1(10)"), a second sample of the mixture was stirred at medium speed for 12 minutes ("Amylettes Product 1(12)"), and a third sample of the mixture was stirred at medium speed for 15 minutes ("Amylettes Product 1(15)"). The temperature was maintained at 63° C. for the enzyme treatment. As shown in FIG. 3B, the optimal activity of FUNGAMYL 800 is within 40-60° C. At 63° C. the enzyme activity is restrained to less than 50% relative activity. The steam was turned on to heat the kettle to 85° C. to fully denature and inactivate the enzyme. After the enzyme was inactivated, the temperature was reduced to 65° C. At this stage, the composition can be packaged for cool storage.

Figure 4A:
FIGS. 4A-G describe Amylettes Product 1, according to one or more embodiments of the present disclosure. (A) is a color image of Amylettes Product 1(10) after addition of iodine (20° C.); (B) is a graph showing speed dependent changes in dynamic viscosity of Amylettes Product 1(10) at 20° C.; (C) is a color image of Amylettes Product 1(15) after addition of iodine (20° C.); (D) is a graph showing speed dependent changes in dynamic viscosity of Amylettes Product 1(15) at 20° C.; (E), (F), and (G) show the temperature dependent changes in the dynamic viscosity of Amylettes Product 1(10), Amylettes Product 1(12), and Amylettes Product 1(15), respectively.
Figure 4B:
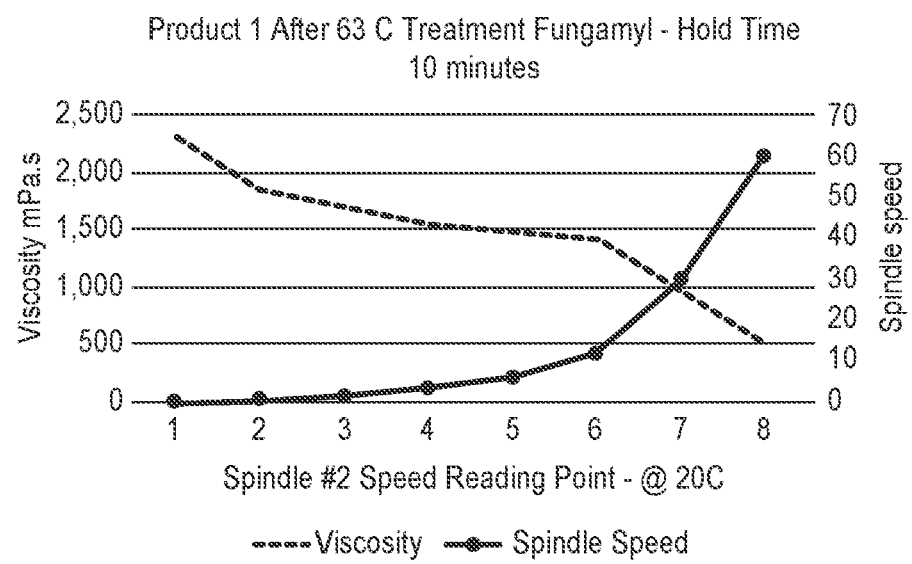

The products were assessed using the color formed upon the interaction between amylose and iodine. The intensity of the color formed by the amylose-iodine complex varies with amylose chain lengths. The relative chain length of amylose can also be determined by the amylose-iodine reaction as the color and $\lambda$max of the complexes change depending on amylose chain length and the helix cavity. The $\lambda$max of the complex increases with increasing amylose degrees of polymerization. Longer chains of amylose exhibit a blue coloration and maintain the coloration for a longer period of time than shorter chains. FIG. 4A shows the dark purple coloration of Product 1(10) after addition of a solution of potassium iodine. An initial bright blue coloration appeared and disappeared quickly. FIG. 4B shows the change in dynamic viscosity of a 20% w/v solids content composition of Amylettes Product 1(10) at 20° C. with increasing spindle speed, measured using a Rotary Viscometer (KUN-HEWUHUA, model DNJ-8S), having an accuracy of +/−5%, spindle 2. The 20% solids composition of Amylettes Product 1(10) exhibited shear-thinning behavior. The data are provided in TABLE 1.

TABLE 1

Dynamic Viscosity of Amylettes Product 1 with 10 minute fungal amylase treatment, spindle 2 at 20° C. (20 wt % solids).

| Speed (rpm) | Spindle | Viscosity (mPa · s) | Temperature (° C.) | % scale |
|---|---|---|---|---|
| 0.3 | 2 | 2300 | 20 | 2.2 |
| 0.6 | 2 | 1850 | 20 | 3.7 |
| 1.5 | 2 | 1680 | 20 | 8.4 |
| 3 | 2 | 1540 | 20 | 15.4 |
| 6 | 2 | 1470 | 20 | 29.4 |
| 12 | 2 | 1400 | 20 | 56 |
| 30 | 2 | 997 | 20 | 99.9 |
| 60 | 2 | 499.5 | 20 | 99.9 |

Figure 4C:
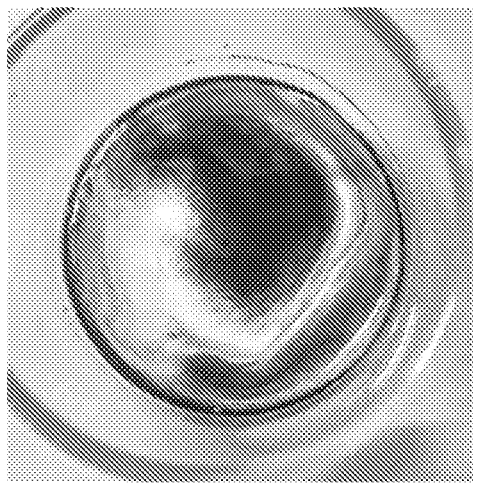
Figure 4D:
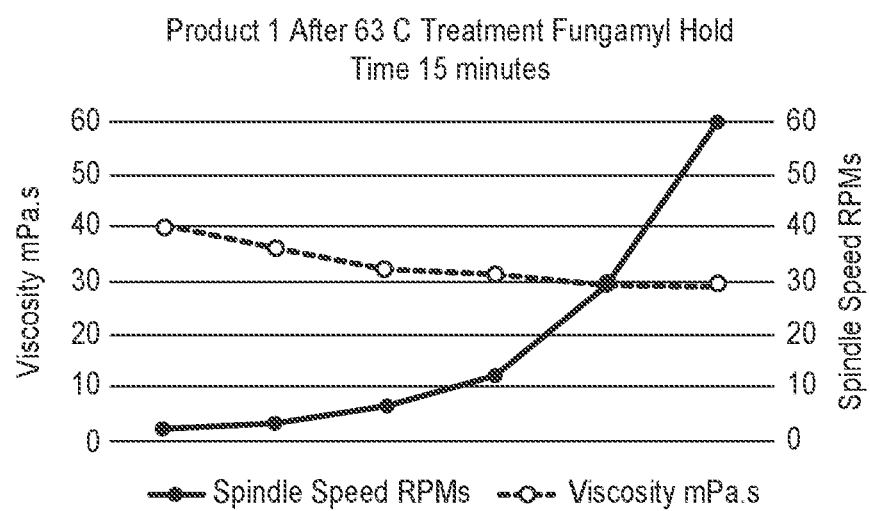

FIG. 4C shows the bright purple coloration of Amylettes Product 1(15). The difference in color relative to Amylettes Product 1(10) suggests the duration enzymatic treatment can be manipulated to impart in distinct degrees of modified amylose chain shortening. FIG. 4D shows the change in dynamic viscosity of a 20% w/v solids content composition of Amylettes Product 1(15) with increasing spindle speed, measured using the same Rotary Viscometer (spindle 1). The composition exhibited shear-thinning behavior. The data are provided in TABLE 2.

TABLE 2

Dynamic Viscosity of Amylettes Product 1 with 15 minute fungal amylase treatment, spindle 1 at 68-75° C. (20 wt % solids).

| Speed (rpm) | Spindle | Viscosity (mPa · s) | Temperature (° C.) | % scale |
|---|---|---|---|---|
| 1.5 | 1 | 40 | 75 | 1.0 |
| 3 | 1 | 36 | 75 | 1.8 |
| 6 | 1 | 32 | 75 | 3.2 |
| 12 | 1 | 31 | 70 | 6.3 |
| 30 | 1 | 29 | 68 | 14.0 |
| 60 | 1 | 29 | 66 | 29.0 |

Figure 4E:
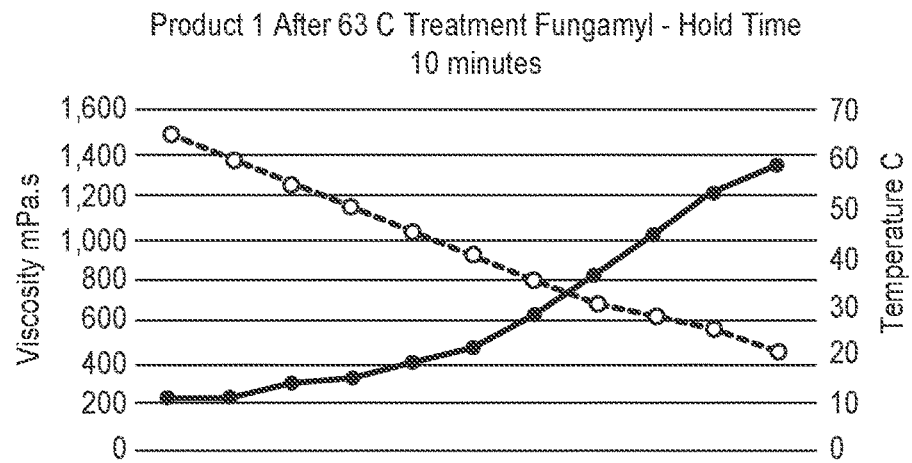
Figure 4F:
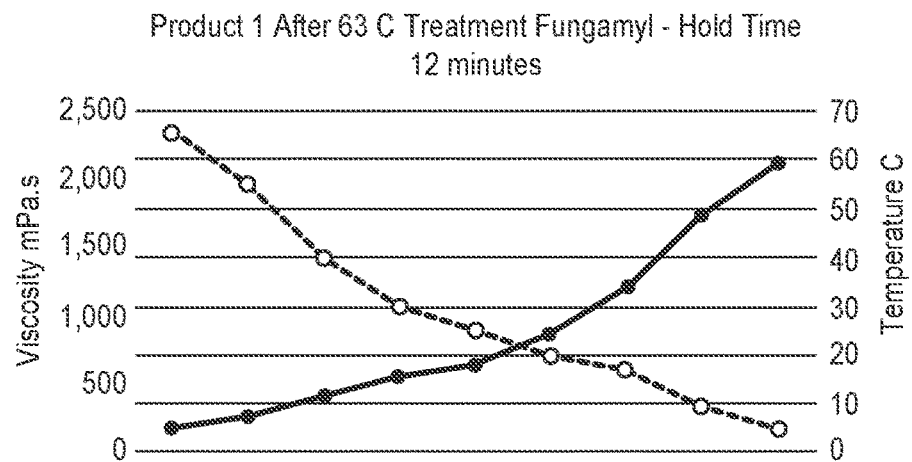
Figure 4G:
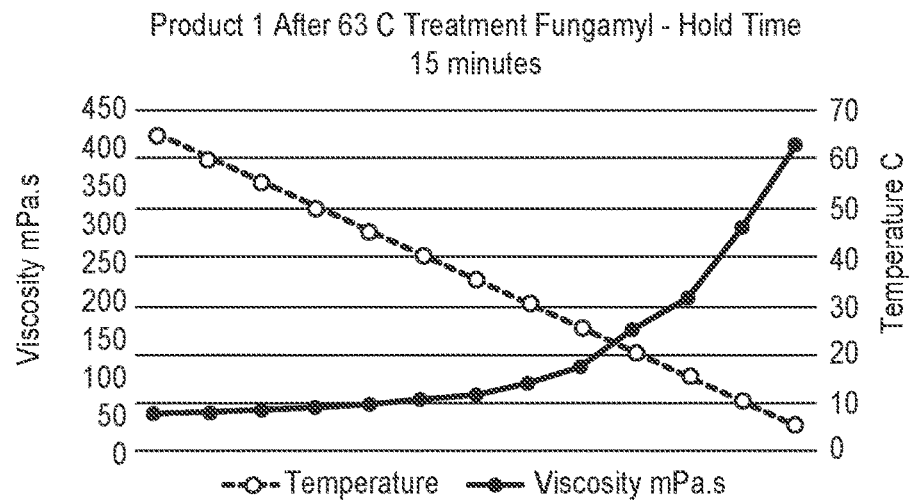

FIG. 4E-G show the change in dynamic viscosity of a 20% w/v solids content composition of Amylettes Product 1(10), Amylettes Product 1(12), and Amylettes Product 1(15), respectively, with increasing temperature and constant spindle speed (12 rpm). The data are provided in TABLES 3-5.

TABLE 3

Dynamic Viscosity of Amylettes Product 1 with 10 minute fungal amylase treatment (20 wt % solids).

| Speed (rpm) | Spindle | Viscosity (mPa · s) | Temperature (° C.) | % scale | time |
|---|---|---|---|---|---|
| 12 | 2 | 232 | 65 | 9.3 | 1:00 |
| 12 | 2 | 232 | 60 | 9.3 |  |
| 12 | 2 | 307.5 | 55 | 12.3 |  |
| 12 | 2 | 325 | 50 | 13 |  |
| 12 | 2 | 405 | 45 | 16.2 | 1:13 |
| 12 | 2 | 472.5 | 40 | 18.9 | 1:25 |
| 12 | 2 | 630 | 35 | 25.1 | 1:47 |
| 12 | 2 | 817 | 30 | 32.5 | 1:58 |
| 12 | 2 | 1020 | 27.3 | 40.8 | 2:22 |
| 12 | 2 | 1210 | 25 | 48.4 | 2:38 |
| 12 | 2 | 1350 | 20 | 54 | 2:05 |

TABLE 4

Dynamic Viscosity of Amylettes Product 1 with 12 minute fungal amylase treatment (20 wt % solids).

| Speed (rpm) | Spindle | Viscosity (mPa · s) | Temperature (° C.) |
|---|---|---|---|
| 12 | 2 | 179 | 65.5 |
| 12 | 2 | 262 | 55 |
| 12 | 2 | 430 | 40 |
| 12 | 2 | 577 | 30 |
| 12 | 2 | 647 | 25 |
| 12 | 2 | 870 | 20 |
| 12 | 2 | 1222 | 17 |
| 12 | 2 | 1750 | 10 |
| 12 | 2 | 2125 | 5 |

TABLE 5

Dynamic Viscosity of Amylettes Product 1 with 15 minute fungal amylase treatment (20 wt % solids).

| Speed (rpm) | Spindle | Viscosity (mPa · s) | Temperature (° C.) |
|---|---|---|---|
| 12 | 1 | 43.5 | 65 |
| 12 | 1 | 47.5 | 60 |
| 12 | 1 | 51 | 55 |
| 12 | 1 | 55 | 50 |
| 12 | 1 | 57.5 | 45 |
| 12 | 1 | 66.6 | 40 |
| 12 | 1 | 71.5 | 35 |
| 12 | 1 | 86 | 30 |
| 12 | 1 | 109 | 25 |
| 12 | 1 | 159.5 | 20 |
| 12 | 1 | 201.5 | 15 |
| 12 | 1 | 295 | 10 |
| 12 | 1 | 405 | 5 |

Figure 5A:
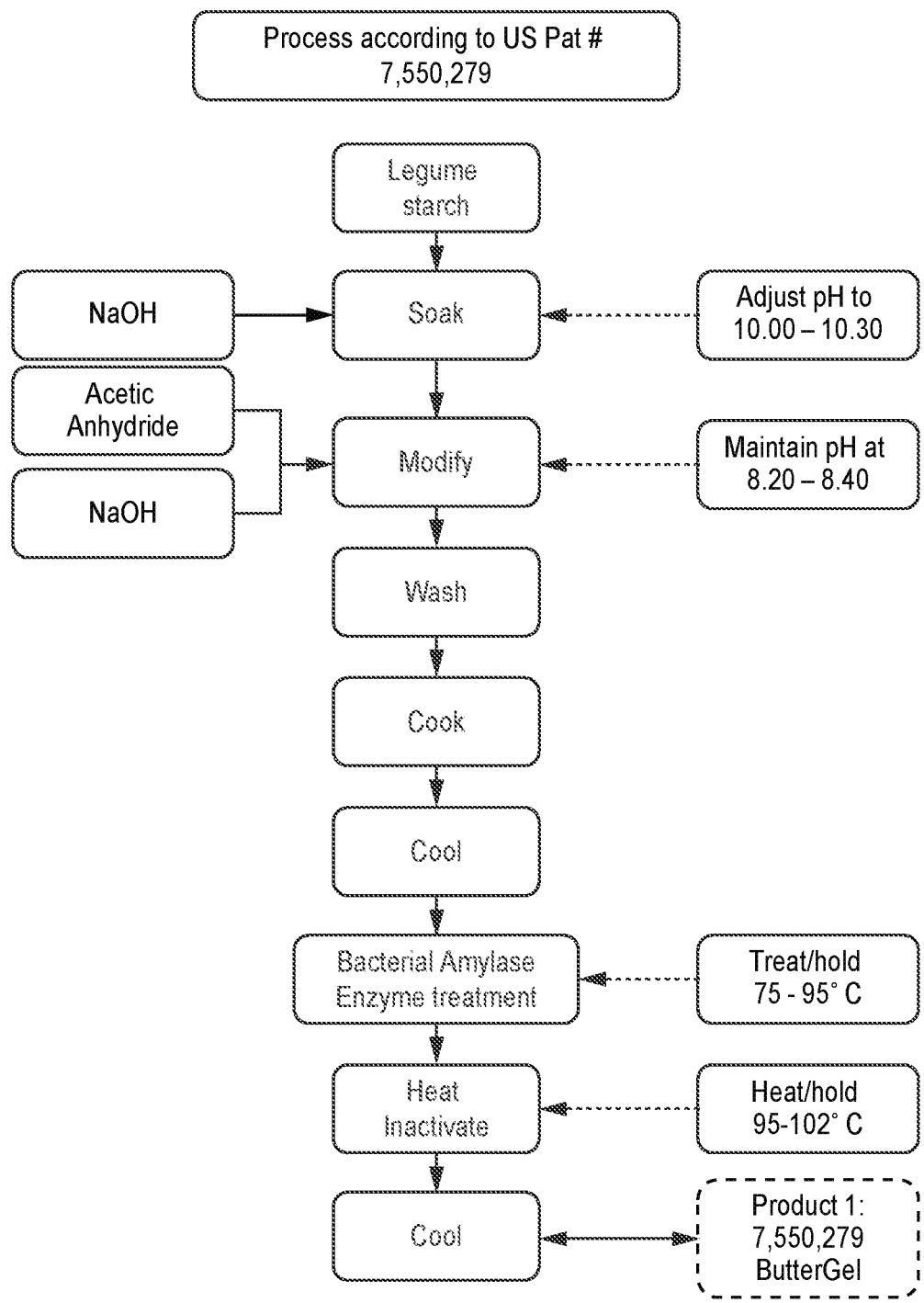
FIGS. 5A-D describe "ButterGel", a modified starch-derived gel (20 wt % solids) according to a prior art method (U.S. Pat. No. 7,550,279) for comparison with clathrate-forming compositions according to one or more embodiments of the present disclosure. (A) is a flowchart describing materials and methods for providing "ButterGel"; (B) is a color image of the chilled gel; (C) is a color image of the melted gel after the addition of iodine; (D) is graph showing a temperature dependent change in the dynamic viscosity of "ButterGel".
Figure 5B:
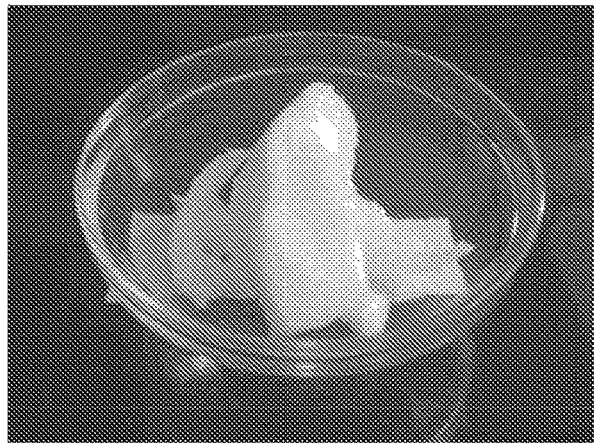
Figure 5C:
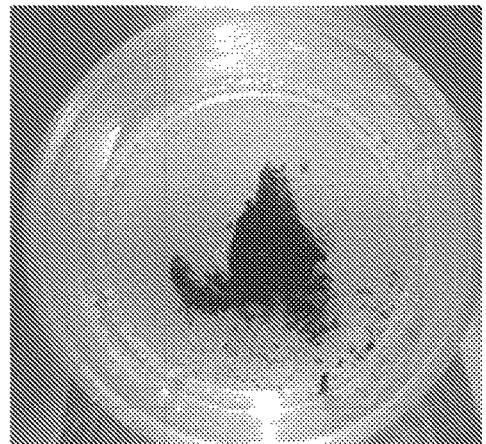
Figure 5D:
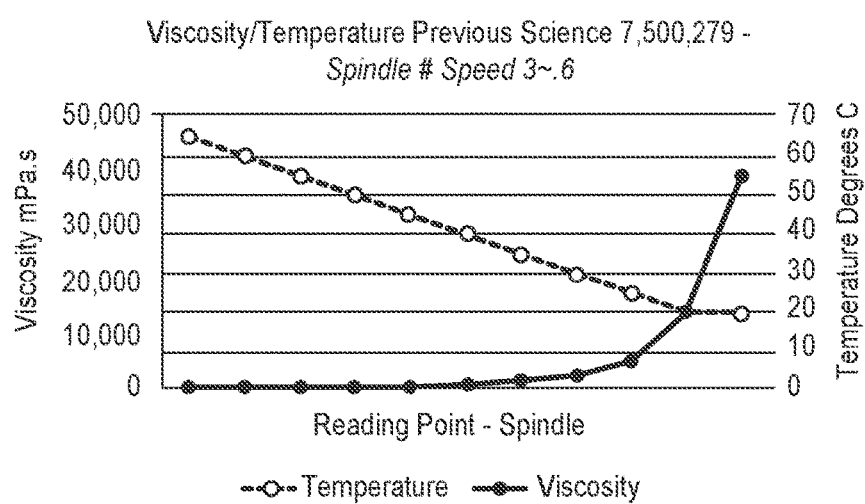

These result suggest that controlled enzymatic hydrolysis of starch can be used to obtain various valuable hydrolysates with different compositions. Properties of the Amylettes Products 1 were compared to the properties of a partially hydrolyzed modified starch prepared according to the process of U.S. Pat. No. 7,550,279, as summarized in FIG. 5A. FIG. 5B shows the prior art product is an opaque white solid at 4° C. FIG. 5C shows the prior art product after melting is a viscous gel (20° C.), which exhibits blue-black coloration after the addition of potassium iodide solution. The iodine test result is indicative of significant long chain amylose content. While not wishing to be bound by theory, it is believed that the prior art product includes greater long chain amylose content than Amylettes Product 1, and the long chain amylose molecules contributed to the texture of the foods described therein. The composition differences occur, in part, because the prior art process conditions do not achieve the same degree of granule permeation during soaking, and therefore, the granules have a reduced susceptibility to the bacterial amylase. FIG. 5D shows the change in viscosity of a 20% w/v solids content composition of prior art product with increasing temperature and different speeds at 20° C., as measured using the same Rotary Viscometer as previous measurements. Viscosity measurements can also describe transition state of these thermoreversible gels during melting/solidification. The composition exhibited a maximum viscosity of 39200 mPa·s (at 0.6 rpm, 20° C., spindle 2) which is also indicative of significant amylose content. The data are provided in TABLE 5.

TABLE 5

Dynamic viscosity of prior art product (20 wt % solids).

| Speed (rpm) | Spindle | Viscosity (mPa · s) | Temperature (° C.) | % scale | time |
|---|---|---|---|---|---|
| 3 | 2 | 460 | 65 | 4.6 | 1:00 |
| 3 | 2 | 469.9 | 60 | 4.7 | |
| 3 | 2 | 610 | 55 | 6.1 | |
| 3 | 2 | 690 | 50 | 6.9 | 1:17 |
| 3 | 2 | 940 | 45 | 9.4 | 1:20 |
| 3 | 2 | 1360 | 40 | 13.6 | 1:28 |
| 3 | 2 | 1970 | 35 | 19.7 | 1:37 |
| 3 | 2 | 2990 | 30 | 29 | 1:51 |
| 3 | 2 | 5620 | 25 | 56.2 | 2:09 |
| 1.5 | 2 | 14600 | 20 | 72.8 | 2:54 |
| 0.6 | 2 | 39200 | 20 | 78 | 4:01 |

These results suggest that the use of restrained enzymes provides shorter chain amylose molecules, which have a wider range of functionalities that the prior art product including a tunable melt rate and temperature profile. Without wishing to be bound by theory, the different properties can be the result of more effective placement of protective ester groups as a result of the relatively more alkaline pH of the soak solution and longer duration of the soaking period and more targeted enzyme hydrolysis.

Example 2: Restrained Enzyme for Engineering Amylose Chain Length—Amylettes Product 2

Figure 6:
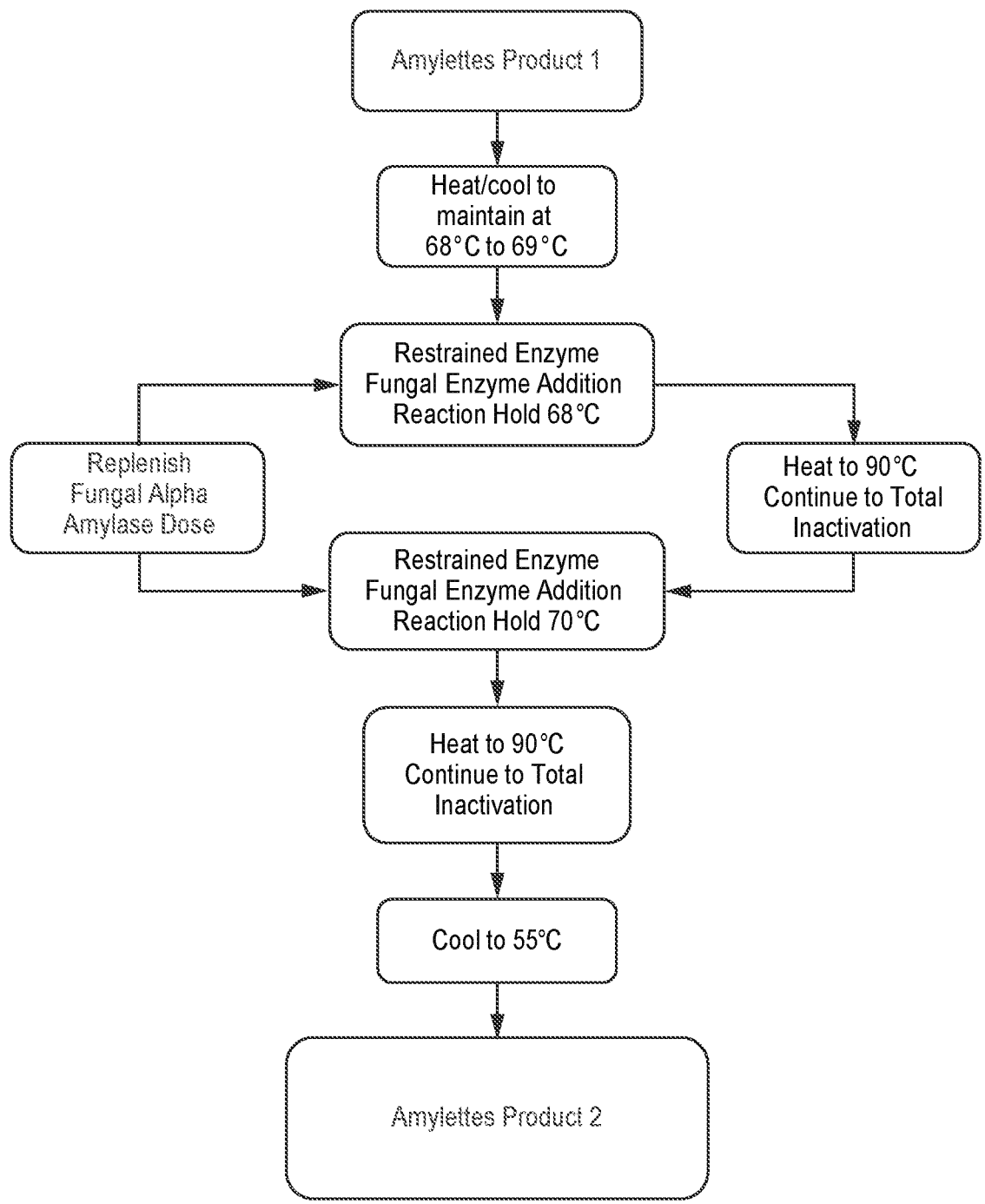
FIG. 6 is a flowchart describing materials and methods for preparing a second clathrate-forming composition, referred to as "Amylettes Product 2", according to one or more embodiments of the present disclosure.

The following example describes an embodiment of Process 2, shown in FIG. 6.

A portion of Amylettes Product 1 prepared according to the method of Example 1 (approximately 1040.5 kg (2294 lb)), using a enzyme treatment of about 14-15 minutes duration was introduced to a double action scraped surface steam jacketed kettle. The composition was cooled to 69° C. The temperature was not allowed to exceed 69° C. to avoid premature inactivation of the enzyme. 5 g FUNGAMYL 800 was added while stirring at high speed. The mixture was stirred for 10 minutes, during which the temperature was maintained at 68-69° C.

In some cases, additional 5 g FUNGAMYL 800 was added while stirring at high speed to replenish the activity lost due to denaturation. The mixture was again stirred for 10 minutes, during which the temperature was maintained at 68-69° C. The temperature was raised to 70° C. before the additional enzyme was added to inactivate the residual enzyme activity. Alternatively, further chain shortening and/or greater uniformity was achieved by adding additional 5 g FUNGAMYL 800 while stirring at high speed, however, greater restraint of the enzyme was achieved by maintaining the temperature at 70° C. for 10 minutes, while stirring.

After the desired degree of chain shortening was achieved, the kettle was heated to 85-90° C. for complete enzyme inactivation.

Figure 7A:
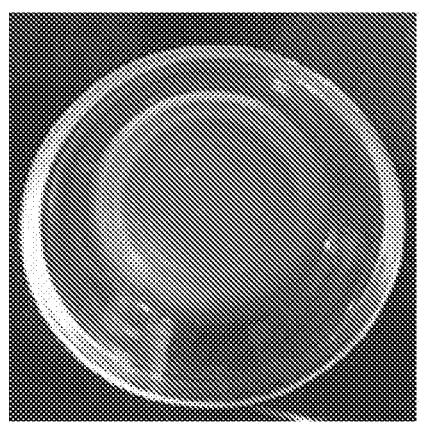
FIGS. 7A-D describe Amylettes Product 2 (20 wt % solids), according to one or more embodiments of the present disclosure. (A) shows a color image of Amylettes Product 2 at 4° C.; (B) shows a color image of Amylettes Product 2 after addition of iodine; (C) and (D) show speed dependent changes in the dynamic viscosity of Product 2 at 12.5° C. and 60° C., respectively.
Figure 7B:
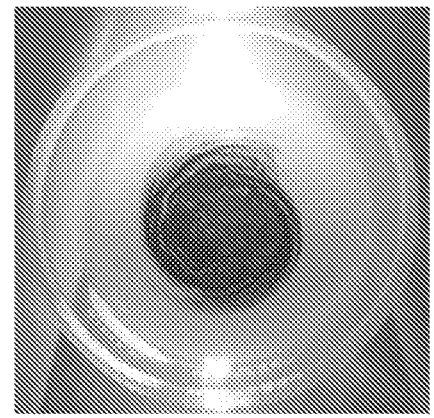
Figure 7C:
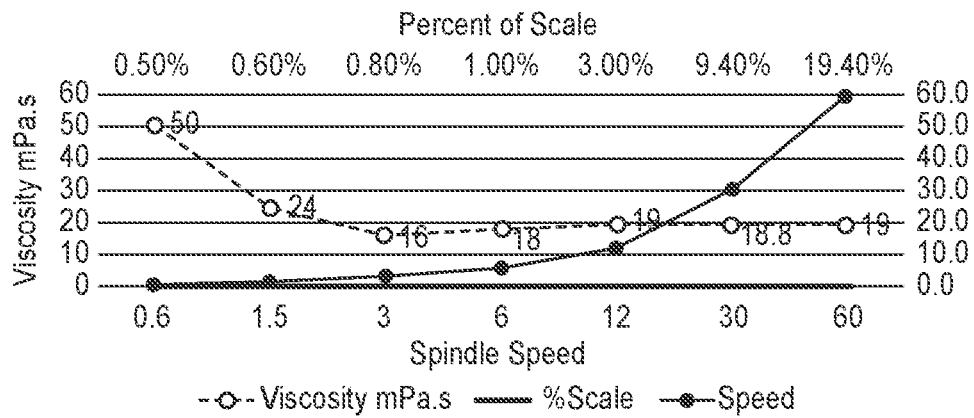
Figure 7D:
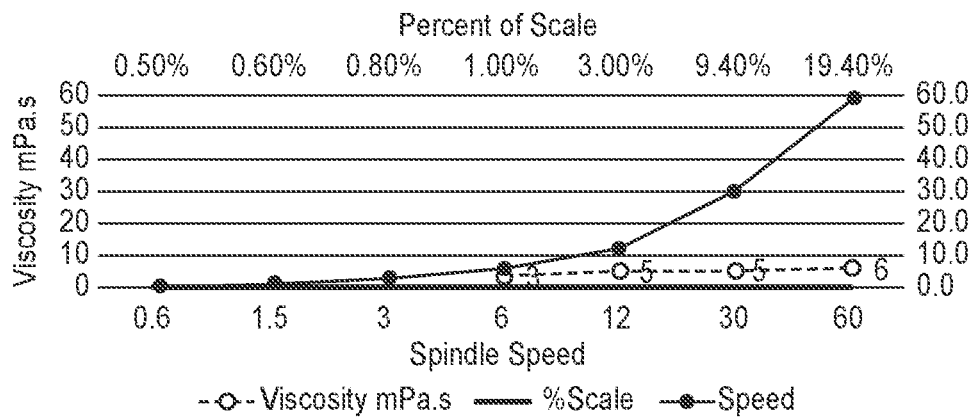

FIG. 7A shows Amylettes Product 2 (resulting from a first thinning at 63° C., a second thinning at 68° C., with enzyme replenishment after heating to 70° C., is a cloudy gel when chilled (4° C.). FIG. 7B shows the red-purple coloration of Amylettes Product 2 after addition of a solution of potassium iodine. FIGS. 7C and 7D show the change in viscosity of a 20% w/v solids content composition of Amylettes Product 2 with increase spindle speed measured using the same Rotary Viscometer (spindle 1) at 12.5° C. and 60° C., respectively. The data are provided in TABLES 6 and 7.

TABLE 6

Dynamic Viscosity of Amylettes Product 2 at 12.5° C. (20 wt % solids).

| Speed (rpm) | Spindle | Viscosity (mPa · s) | Temperature (° C.) | % scale |
|---|---|---|---|---|
| 0.6 | 1 | 50 | 12.5 | 0.50% |
| 1.5 | 1 | 24 | 12.5 | 0.60% |
| 3 | 1 | 16 | 12.5 | 0.80% |
| 6 | 1 | 18 | 12.5 | 1.00% |
| 12 | 1 | 19 | 12.5 | 3.00% |
| 30 | 1 | 18.8 | 12.5 | 9.40% |
| 60 | 1 | 19 | 12.5 | 19.40% |

TABLE 7

Dynamic Viscosity of Amylettes Product 2 at 60° C. (20 wt % solids).

| Speed (rpm) | Spindle | Viscosity (mPa · s) | Temperature (° C.) | % scale |
|---|---|---|---|---|
| 0.6 | 1 | | 60 | |
| 1.5 | 1 | | 60 | |
| 3 | 1 | | 60 | |
| 6 | 1 | 3 | 60 | 0.03% |
| 12 | 1 | 5 | 60 | 1.00% |
| 30 | 1 | 5 | 60 | 2.50% |
| 60 | 1 | 6 | 60 | 6.30% |

Example 3: Hydrolysis of Amylopectin Components and Conversion of Extraneous Cell Material—Amylette Composition 3

Figure 8:
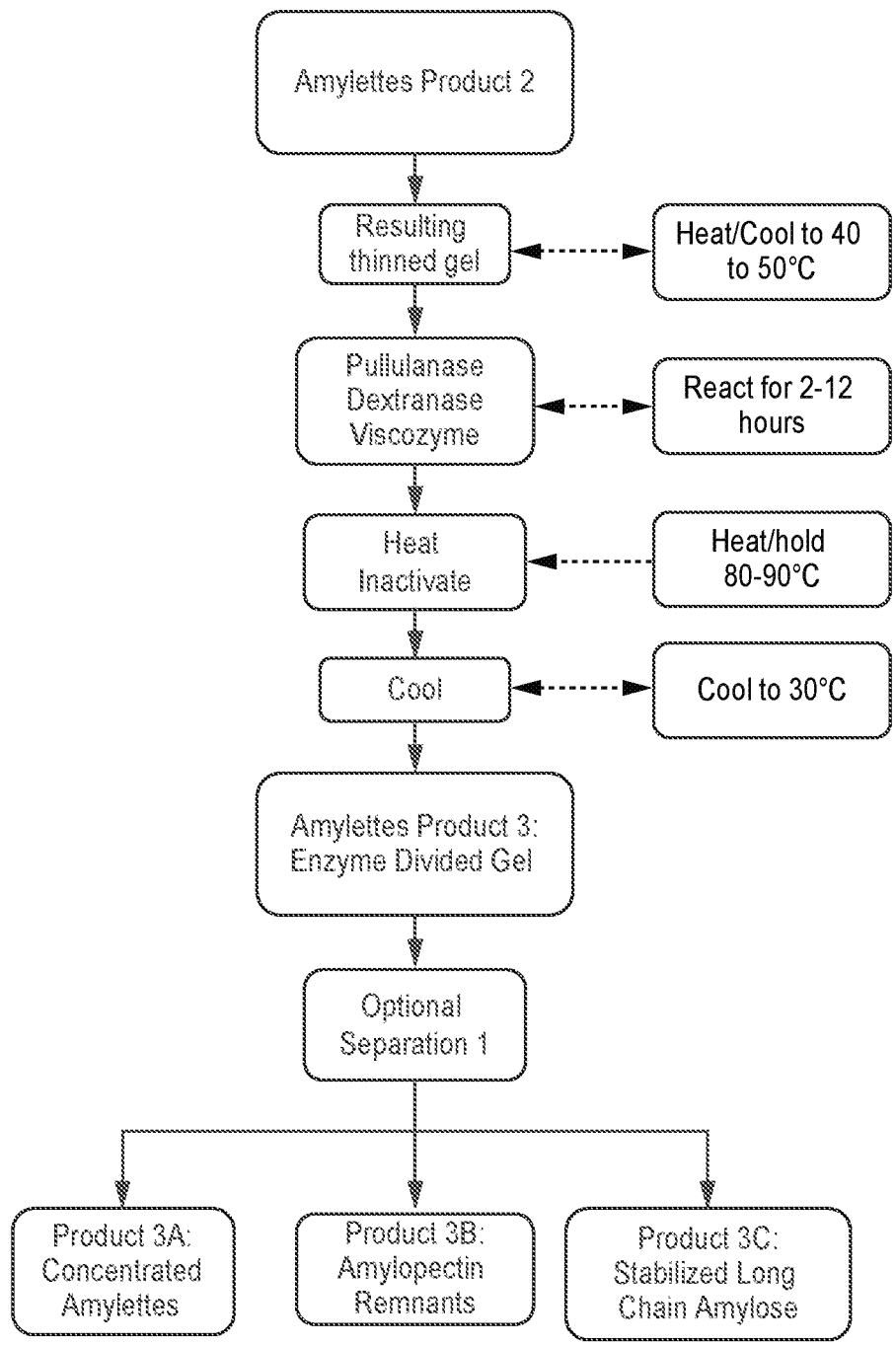
FIG. 8 is a flowchart describing materials and methods for preparing a third clathrate-forming composition, referred to as "Amylettes Product 3", which can be separated into Products 3A, 3B and 3A, according to one or more embodiments of the present disclosure.

The following example describes an embodiment of Process 3, shown in FIG. 8.

A portion of Amylettes Product 2 (approximately 1040.5 kg (2294 lb)) was introduced to a double action scraped surface steam jacketed kettle, cooled and maintained at 48° C. Each of the following were separately added, while stirring at high speed: 100 g PROMOZYME, a pullulanase enzyme commercially available from Novozyme Corp, 25 g DEXTRANASE L, a dextranase enzyme commercially available from BIO-CAT and 50 g VISCOZYME, a multi-enzyme complex containing carbohydrases to hydrolyze pectin and hemicellulose that may have been present in the starting material, which is commercially available from Novozyme Corp. The mixture was stirred for 5 hours, during which the temperature was maintained within the range of 40 to 50° C.

After the desired degree of hydrolysis was achieved, the kettle was heated to 80-90° C. for complete enzyme inactivation. The kettle was then cooled to 30° C.

After chilling for 24 hours at 4° C., the chilled product (Amylettes Product 3) was separated into three fractions by centrifugation: Amylettes Product 3A, which is enriched in amylettes; Amylettes Product 3B, which includes remnants of amylopectin; and Modified Amylose Product 3C, which includes stabilized (i.e., acetylated) long chain amylose.

Figure 9E:
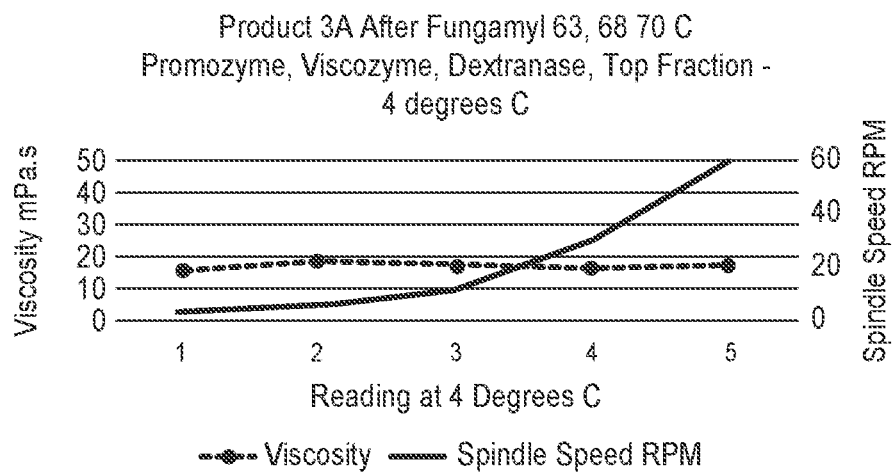
Figure 9F:
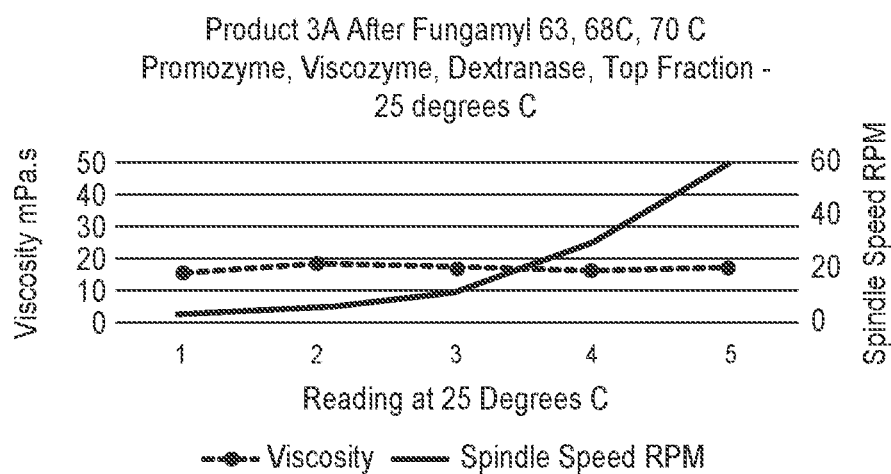

FIGS. 9A and 9C show translucent appearance of chilled Amylettes Products 3A and 3B (20 wt % solids at 4° C.), respectively. FIGS. 9B and 9D show the red-orange coloration of Amylettes Products 3A and 3B, respectively, after addition of a solution of potassium iodine. The loss of any blue coloration is indicative of the removal of long-chain amylose from Amylettes Product 3. The viscosity was measured using a Rotary Viscometer as described previously (spindle 1). FIGS. 9E and 9F show the effect of increasing spindle speed on the viscosity of Product 3A at 4° C. and 25° C., respectively. The data are shown in TABLES 8 and 9.

TABLE 8

Speed-dependent changes in Dynamic Viscosity of Amylettes Product 3A at 4° C. (20 wt % solids)

| Speed (rpm) | Spindle | Viscosity (mPa · s) | Temperature (° C.) | % scale |
|---|---|---|---|---|
| 3 | 1 | 16 | 4 | 0.09 |
| 6 | 1 | 19 | 4 | 1.9 |
| 12 | 1 | 17 | 4 | 3.4 |
| 30 | 1 | 17 | 4 | 8.6 |
| 60 | 1 | 17 | 4 | 17.4 |

TABLE 9

Speed-dependent changes in Dynamic Viscosity of Amylettes Product 3A at 25° C. (20 wt % solids).

| Speed (rpm) | Spindle | Viscosity (mPa · s) | Temperature (° C.) | % scale |
|---|---|---|---|---|
| 3 | 1 | 2 | 25 | 0.09 |
| 6 | 1 | 4 | 25 | 1.9 |
| 12 | 1 | 5 | 25 | 3.4 |
| 30 | 1 | 7 | 25 | 8.6 |
| 60 | 1 | 9.6 | 25 | 17.4 |

These results suggest the effect of amylopectin on the clathrate-forming compositions can be controlled with the combined use of pullulanase and dextrinase.

Example 4: Conversion of Amylopectin Remnants to Glucose—Amylettes Composition 4

Figure 10A:
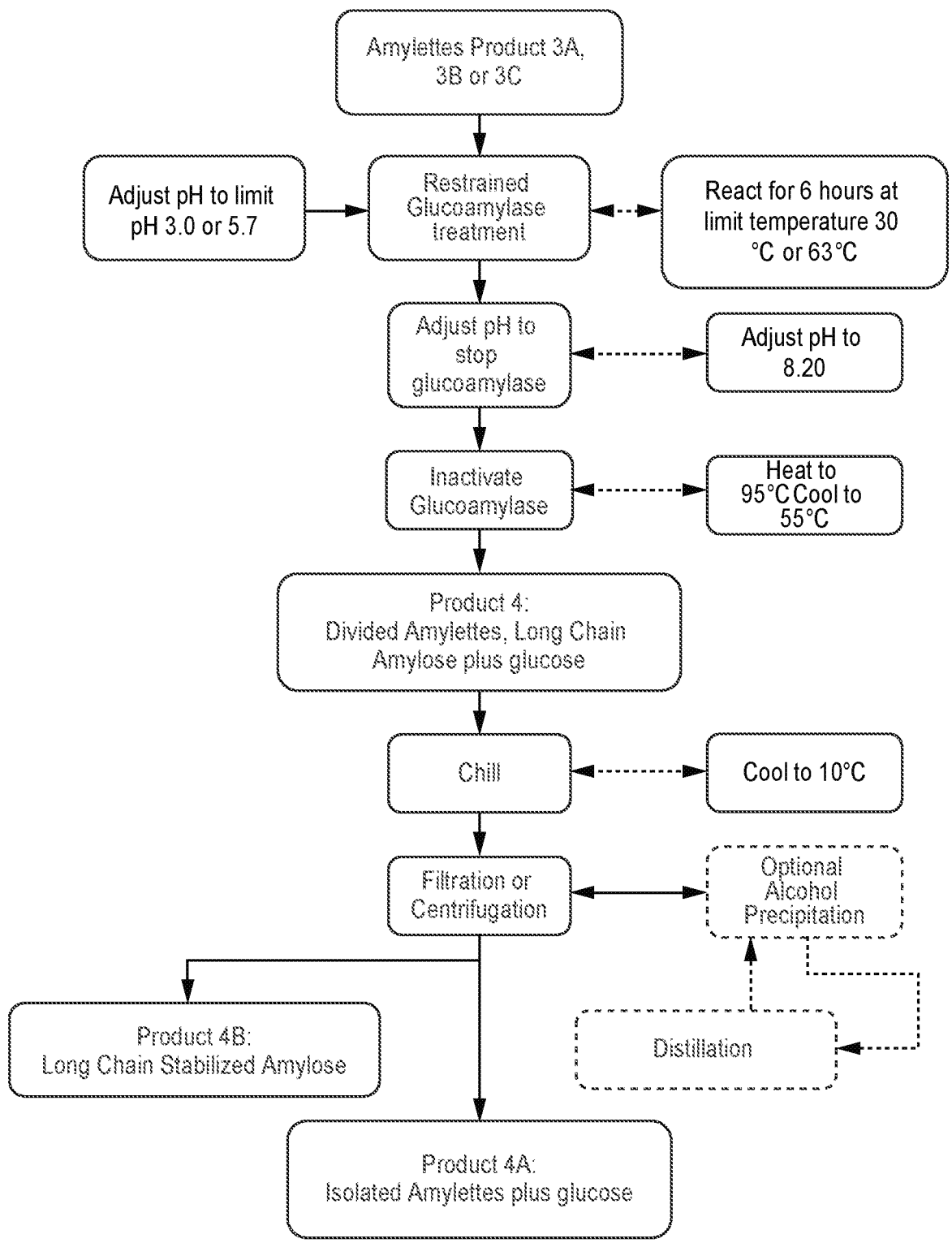
FIGS. 10A-C describe materials and methods for preparing a fourth clathrate-forming composition comprising amylettes and glucose, referred to as "Amylettes Product 4A", and a first wrapping composition comprising esterified long chain amylose, referred to as "Long Chain Stabilized Amylose Product 4B", according to one or more embodiments of the present disclosure. (A) is a flowchart showing preparation of Amylettes Product 4A and Long Chain Stabilized Amylose Product 4B; (B) is a graph showing the effect of temperature on the relative activity of a amylopectin degrading enzyme (glucoamylase) sold under the tradename ENZECO® (Enzyme Development Corp.); (C) is a graph showing the effect of pH and temperature on the relative activity of the glucoamylase enzyme.
Figure 10B:
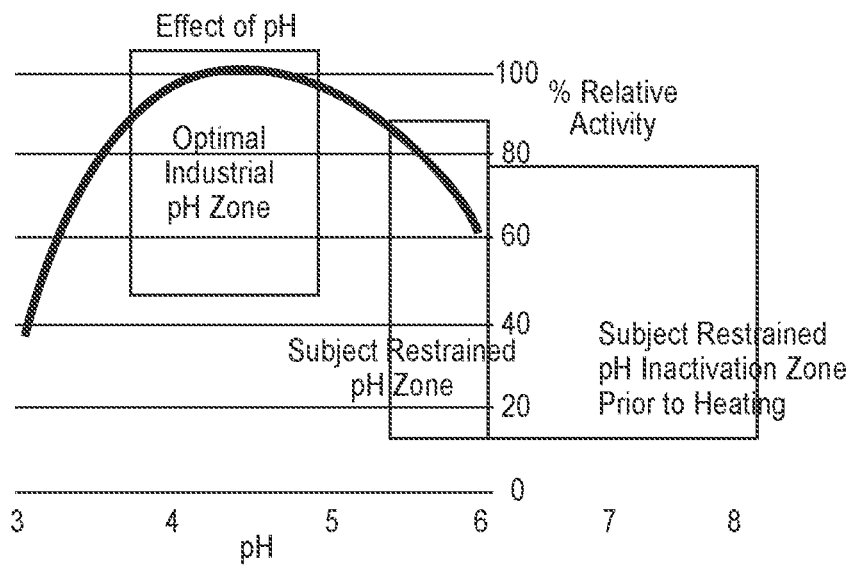
Figure 10C:
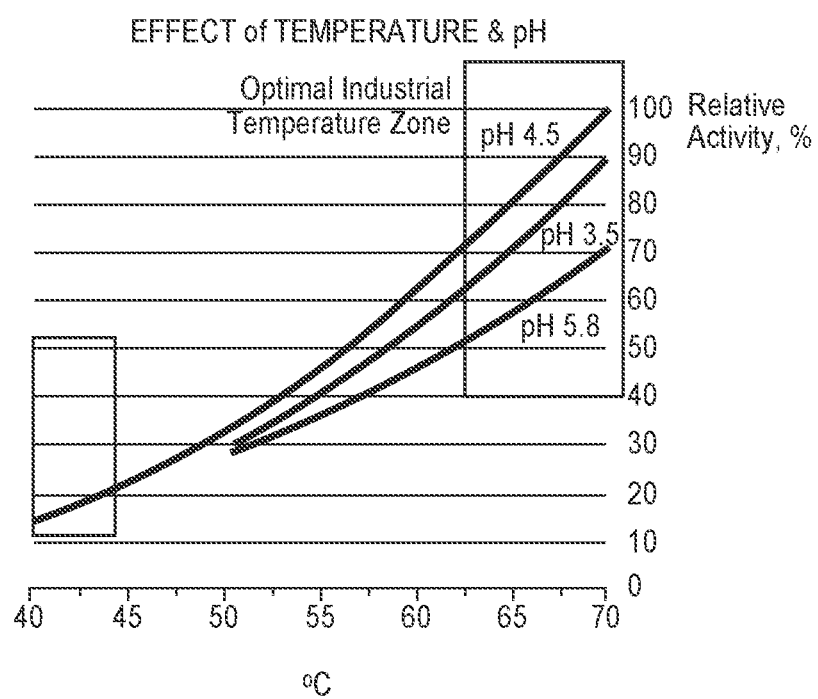

The following example describes an embodiment of Process 4, shown in FIG. 10A.

A portion Amylettes Product 3 (1750 g) was introduced to a stirring reactor reaction vessel with temperature control maintained at 63° C. A citric acid solution was slowly added to the hydrolyzed product to provide a pH of 4.9. Then 30-35 g ENZENCO® GLUCOAMYLASE, a glucoamylase enzyme derived from A. niger, with little protease or amylase side activity present, commercially available from Enzyme Development Corp., was added. The mixture was stirred for 3-6 hours, during which the temperature was maintained at 63° C. The reactor was then heated to 85° C. for enzyme inactivation. After the enzyme was inactivated, the temperature was reduced to 55-63° C.

In alternative preparations, the activity of the glucoamylase was restrained by adjusting the pH to 3.0-3.3 or by reacting at a temperature of 40-45° C. See FIGS. 10B-C for relative enzyme activity at different pH and pH/temperature ranges.

The glucoamylase treated product (Amylettes Product 4) was cooled to 10° C. and separated into two fractions by filtration or centrifugation: (1) Amylettes Product 4A, which is enriched in amylettes and glucose; and (2) Modified Amylose Product 4B, which includes acetylated (i.e., stabilized) long chain amylose.

Amylettes Product 4A was a clear fluid, which remained fluid and clear at room temperature. When chilled for several days, Amylettes Product 4A became opaque, but remained fluid. Transparency was restored by reheating.

Example 5: Transesterification of Lipid onto Amylose—Amylettes Product 5

Figure 11:
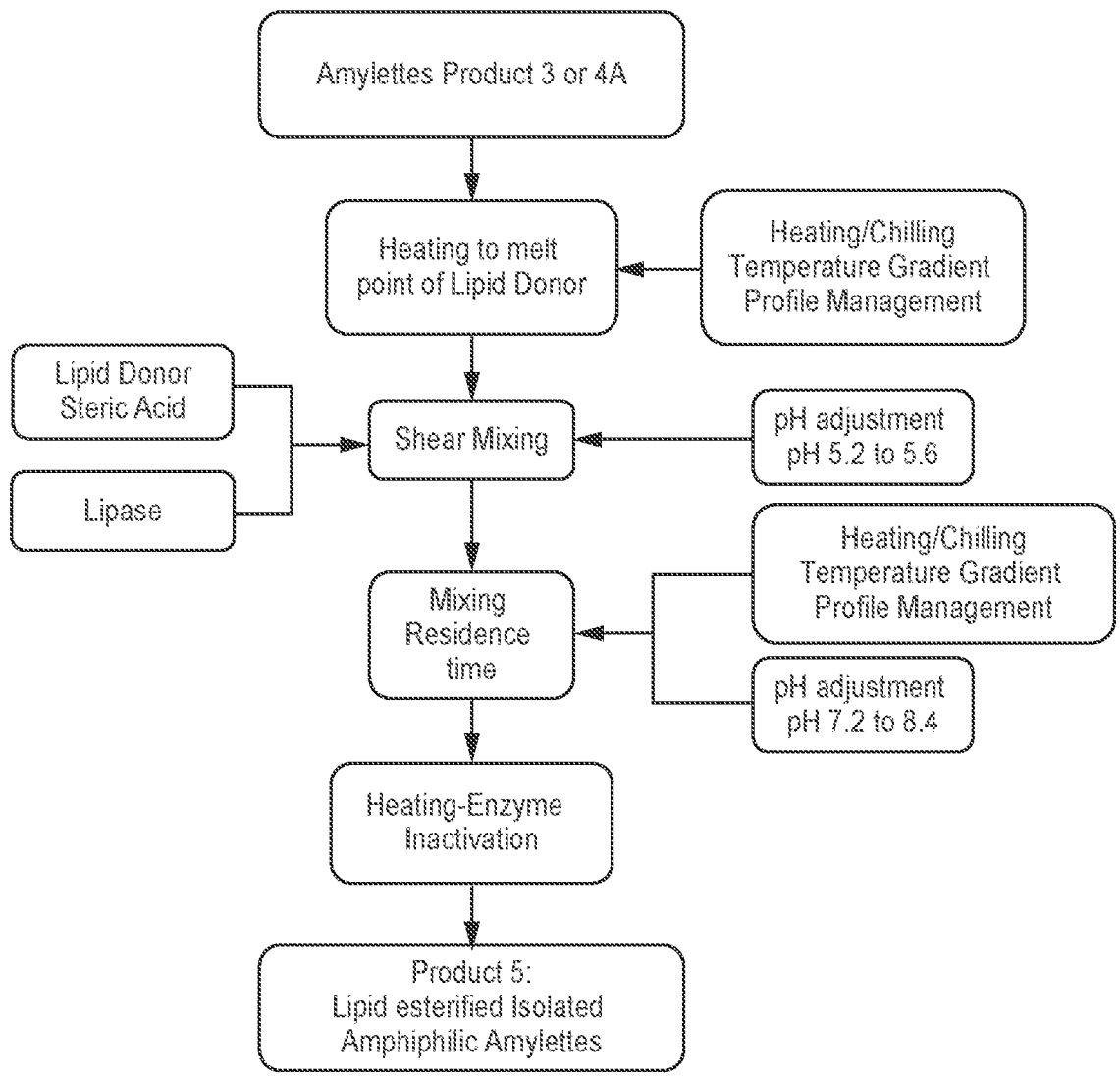
FIG. 11 is a flowchart describing materials and methods for preparing a fifth clathrate-forming composition, comprising lipid esterified amylettes, referred to as "Amylettes Product 5", according to one or more embodiments of the present disclosure.

The following example describes an embodiment of Process 5 shown in FIG. 11.

A portion of Amylettes Product 3 or 4A (1750 g, consisting of 350 g solids and 1400 g water) was introduced to a stirring reactor reaction vessel with temperature control. 31.5 g of the lipid donor steric acid was added, the pH was maintained at 5.2-5.8, and the mixture was heated to 70° C. to melt the lipid donor. High shear mixing was employed to form stearic acid/amylettes product clathrates. The mixture was cooled to 45° C., the pH was adjusted to 7.2 to 8.4, and 2 g ENZECO® LIPASE CONCENTRATE, an aggressive lipase from Candida cylindracea, commercially available from Enzyme Development Corp., was added. The mixture was stirred for 2 hours at medium shear. After the desired degree of transesterification was achieved, the reactor was heated to 70° C. and held for 20 minutes to inactivate the lipase. The resulting composition of amylette-fatty acid esters was cooled.

Amylettes product 5 includes lipid esterified isolated amphiphilic amylettes that exhibited improved efficacy for forming a molecular dispersion of hydrophobic guest molecules such as cannabidiol (CBD).

Example 6: Preparation of De-Esterified Amylose

Figure 12:
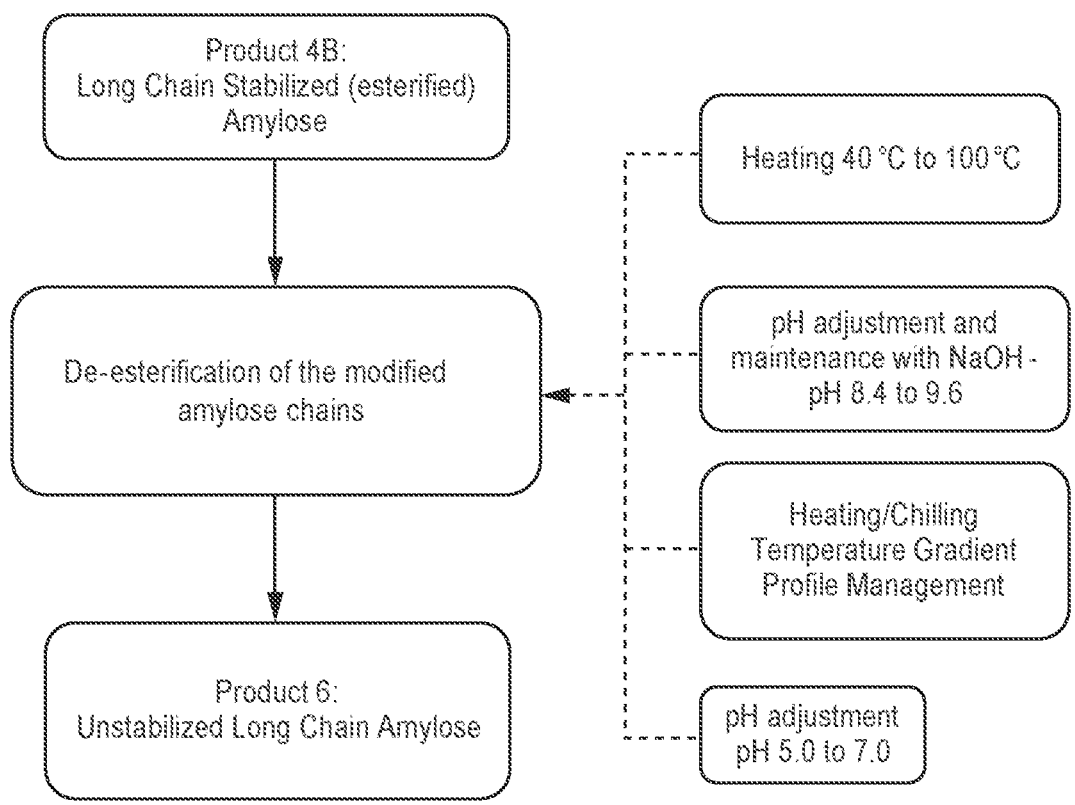
FIG. 12 is a flowchart describing materials and methods for preparing a second wrapping composition, comprising de-esterified long chain amylose, referred to as "Unstabilized Long Chain Amylose Product 6", according to one or more embodiments of the present disclosure.

The following example describes an embodiment of Process 6, shown in FIG. 12.

A portion of Amylettes Products 1, 2, 3, or Modified Amylose Products 3C or 4B (1000 g) was introduced to a stirring reactor reaction vessel with temperature control and heated to 80° C. while stirring. A 10% w/v solution of sodium hydroxide was added while stirring, to maintain a pH of 8.5 until consumption of the base is negligible. The pH is adjusted to 7 and the mixture cooled to 65° C. or 4° C. The de-esterified long chain amylose was concentrated by centrifugation.

De-esterification restored the natural tendency of the amylose to retrograde and closely pack itself. The de-esterified was capable of wrapping itself, in a controllable manner around guest/host complexes, such as amphiphilic guest/host complexes formed with the lipid-esterified amylettes, and imparting a protective shell.

Example 7: Formulations Using Amylettes

Figure 13:
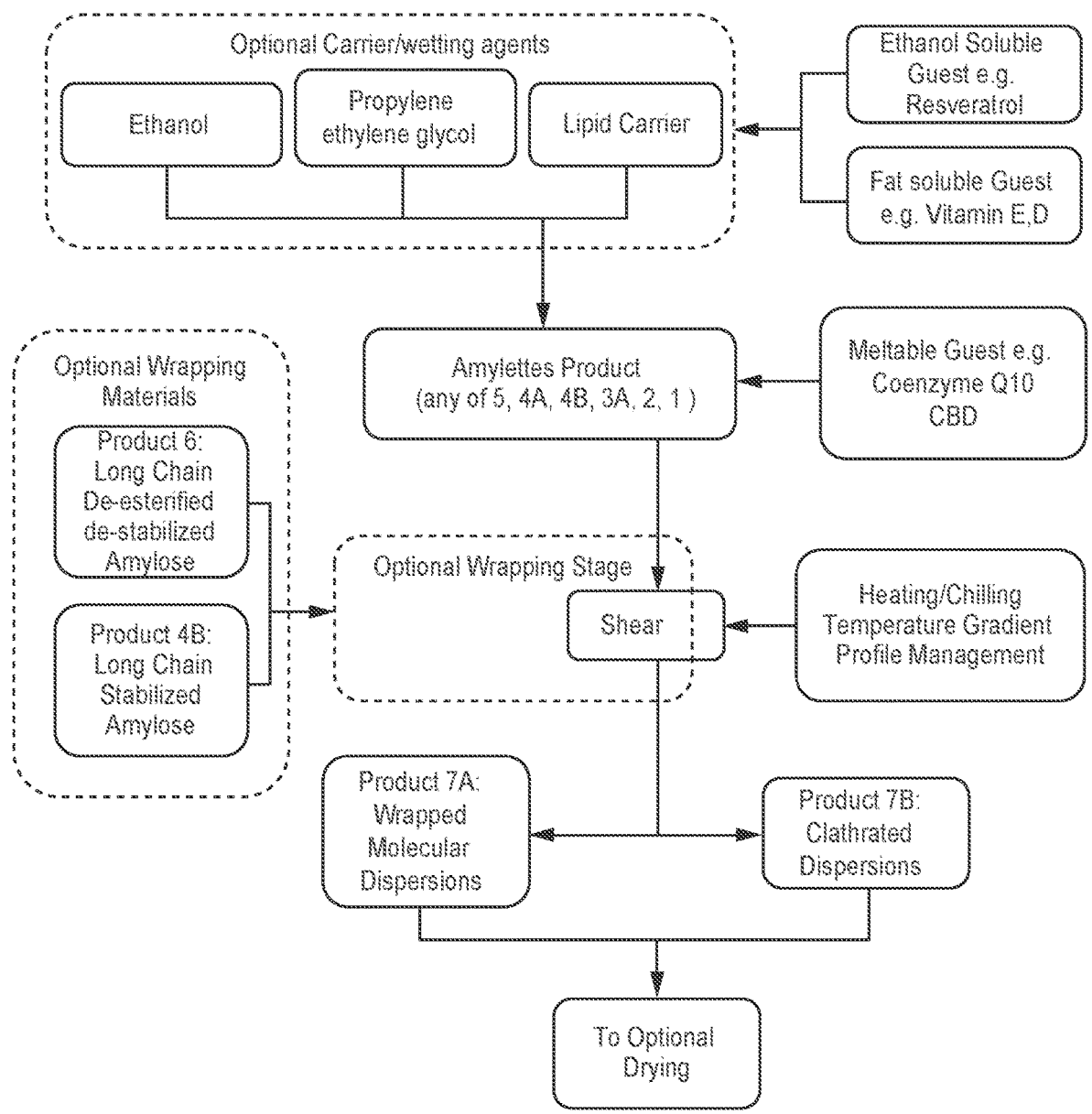
FIG. 13 is a flowchart describing materials and methods for preparing molecular dispersions of various guess molecules, referred to as "Amylettes Products 7A" and "Amylettes Product 7B", according to one or more embodiments of the present disclosure.

The following examples describes embodiments of Process 7, shown in FIG. 13.

A. Wrapped Diindolylmethane (DIM) Complexes

DIM was prepared for association with any of amylettes products 1, 2, 3, 3A, 3B, 4, or 4A by dissolving 5 g DIM powder in 25 g ethanol at 75° C. while stirring.

100 g of an amylettes product (any of 1-4) was heated to 65° C. and subjected to high shear mixing (75%) using a POLYTRON mixer, commercially available from Kinematic. The DIM solution was added to the mixer in a dropwise manner under shear until 30 g was added. Shearing was maintained for 2 minutes. The DIM was transferred from its dissolved state directly into the water-dissolved host molecule thereby forming a clathrate or guest/host complex in water. The mixture was heated to 92° C. while stirring to remove solvent. (This step can be performed at reduced atmosphere). The mixture was then cooled to 65° C.

The DIM complexes were encapsulated by or wrapped in, molecules of de-esterified amylose from Ex. 6 by adding 30 g of reheated de-esterified amylose to the Amylettes-DIM composition 65° C. while stirring. Stirring was continued as the composition was chilled to 5° C. The as prepared wrapped DIM complexes were stored chilled.

B. Quercetin Complexes (I and II)

I. Quercetin was solubilized by adding 0.6 g quercetin powder to 60 g water and heating to 60° C. while stirring. 4.734 g of a 1N NaOH solution was added. A transparent deep red solution was formed.

30 g of a 20% solids Amylettes Products 1, 2, 3, 3A, 3B, 4, or 4A (as prepared in Ex. 1-4) was diluted with 70 g water and heated to 60° C. The diluted composition was subjected to high shear mixing (75%) using a POLYTRON mixer. The quercetin solution was added to the diluted composition in a dropwise manner under shear until all 65.334 g was added. After addition, the mixture was homogenized for 2 minutes. The quercetin was transferred from its melted/dissolved state directly into the water-dissolved host molecule thereby forming a clathrate or guest/host complex in water. The amylettes-Quercetin complexes were then cooled to 10° C. and stored chilled.

II. Quercetin was prepared for association with any of amylettes composition 1-4 by adding 0.6 g quercetin powder to 30 g of a 20% solids amylettes composition (as prepared in Ex. 1-4) which was diluted with 60 g water and comprising sodium bicarbonate and glucono delta-lactone (GDL) to protect the oxygen sensitive active. The mixture was heated to 60° C. while stirring. 4.734 g of a 1N NaOH solution was added. A transparent deep red solution was formed.

30 g of a 20% solids Amylettes Products 1, 2, 3, 3A, 3B, 4, or 4A (as prepared in Ex. 1-4) was diluted with 70 g water and heated to 60° C. The diluted composition was subjected to high shear mixing (75%) using a POLYTRON mixer. The Quercetin solution was added to the diluted composition in a dropwise manner under shear until all 65.334 g was added. After addition, the mixture was homogenized for 2 minutes. The quercetin was transferred from its melted/dissolved state directly into the water-dissolved host molecule thereby forming a clathrate or guest/host complex in water. The amylettes-Quercetin complexes were then cooled to 10° C. and stored chilled.

C. Cannabidiol Oil Isolate (CBD) Molecular Dispersion

A molecular dispersion of CBD is prepared by introducing 180 g of any one of Amylettes Products 1, 2, 3, 3A, 3B, 4, 4A or 5 to a beaker with a stir bar, heating to 74° C. while stirring and adding 20 g CBD. The CBD was allowed to melt on the surface and then the temperature was increased to 75° C. The mixture was stirred until all CBD was emulsified while maintaining temperature. The CBD emulsion was transferred to a POLYTRON high shear mixer in a water bath and subjected to high shear to produce a molecular dispersion of CBD. The temperature was reduced by adding ice to the water bath. The composition was mixed at high shear until a temperature of about 30° C. was achieved. A milky white molecular dispersion was formed.

D. Resveratrol Complexes

Resveratrol was prepared for association with any of Amylettes Products 3-4 by dissolving 5 g Resveratrol powder in 45 g ethanol and heating to 80° C. while stirring. 400 g of an amylettes composition (any of 3-5) was heated to 65° C. and subjected to high shear mixing (75%) using a POLYTRON mixer, commercially available from Kinematic. The DIM solution was added to the amylettes composition under shear in a dropwise manner. After addition, the shearing continued for 2 minutes. The mixture was heated to 92° C. while stirring to remove solvent. The mixture was then chilled.

E. Wrapped Coenzyme Q10 Complexes

A molecular dispersion of Coenzyme Q10 is prepared by introducing 180 g of Amylettes Product 5 to a beaker with a stir bar, heating to 60° C. while stirring and adding 20 g Coenzyme Q10 powder. The Coenzyme Q10 was allowed to melt on the surface, while stirring at medium speed, maintaining the temperature. The mixture was stirred all Coenzyme Q10 was emulsified (a medium emulsion). The Coenzyme Q10 emulsion was transferred to a POLYTRON high shear mixer in a water bath and subjected to high shear for 5 minutes.

The composition was transferred to a beaker in a water bath on a magnetic stir plate. 30 g of the product from example 6 was added to the beaker while stirring. Ice was added to the water bath to begin cooling and the composition was chilled to 5° C. while stirring. The mixture was chilled and stored.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus, the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

What is claimed is:

1. A clathrate-forming composition comprising a plurality of linear glucomonomer chains of about 15 to about 100 D-glucopyranosyl residues linked by α-1,4 linkages, wherein the linear glucomonomer chains are a product of partial amylolysis of a modified starch substrate, wherein the partially amylolyzed product is flowable at temperatures within a range of 4-20° C. at about 20% w/v solids content, wherein at least one of the glucomonomer chains is esterified.

2. The composition of claim 1, wherein the composition is substantially free of amylopectin and remnants of amylopectin.

3. The composition of claim 1, wherein the composition is substantially free of amylose molecules having a chain length greater than 250 glucomonomers.

4. The composition of claim 1, wherein the esterified glucomonomer chain is esterified with an acylating agent, a fatty acid, or a combination thereof.

5. The composition of claim 4, wherein the esterified glucomonomer chain is esterified with a fatty acid selected from the group consisting of saturated or unsaturated straight chain fatty acids having up to 30 carbon atoms, saturated or unsaturated branched fatty acids having 4 to 26 carbon atoms, and a combination thereof.

6. The composition of claim 1, wherein a dynamic viscosity of the product having a solids content of 20% w/v is less than 2300 mPa·s as measured on a rotary viscometer with spindle 1 operated at a speed of about 0.3 rpm at temperatures within a range of 4-20° C.

7. The composition of claim 1, further comprising a hydrophobic guest molecule.

8. The composition of claim 7, wherein the hydrophobic guest molecule is selected from the group consisting of resveratrol, vitamin E, vitamin D, quercetin, diindolylmethane, coenzyme Q10, and cannabidiol (CBD).

9. A kit for forming a clathrate with a hydrophobic guest molecule comprising:
a first container comprising a clathrate-forming composition comprising a plurality of linear glucomonomer chains of about 15 to about 100 D-glucopyranosyl residues linked by α-1,4 linkages, wherein the linear glucomonomer chains are a product of partial amylolysis of a modified starch substrate and wherein the product is flowable at temperatures within a range of 4-20° C. at about 20% w/v solids content;
a second container comprising a hydrophobic guest molecule;
instructions for preparing the clathrate;
a third container comprising a plurality of amylose chains having a degree of polymerization of at least 250; and
instructions for wrapping the clathrate in the amylose chains.

10. A kit for forming a clathrate with a hydrophobic guest molecule comprising:
a first container comprising a clathrate-forming composition comprising a plurality of linear glucomonomer chains of about 15 to about 100 D-glucopyranosyl residues linked by α-1,4 linkages, wherein the linear glucomonomer chains are a product of partial amylolysis of a modified starch substrate and wherein the product is flowable at temperatures within a range of 4-20° C. at about 20% w/v solids content;
instructions for preparing the clathrate with a hydrophobic guest molecule;
a second container comprising a plurality of amylose chains having a degree of polymerization of at least 250; and
instructions for wrapping the clathrate in the amylose chains.

* * * * *